(12) United States Patent
Yong

(10) Patent No.: US 7,374,763 B2
(45) Date of Patent: May 20, 2008

(54) PROTEIN SEQUENCES CONTAINING ANTIGENIZED ANTIBODIES FOR FOOT-AND-MOUTH DISEASE

(75) Inventor: Xie Yong, Kowloon (HK)

(73) Assignee: The Hong Kong University of Science & Technology, Hong Kong (HK)

( * ) Notice: Subject to any disclaimer, the term of this patent is extended or adjusted under 35 U.S.C. 154(b) by 741 days.

(21) Appl. No.: 10/915,121

(22) Filed: Aug. 9, 2004

(65) Prior Publication Data

US 2005/0202024 A1 Sep. 15, 2005

Related U.S. Application Data

(63) Continuation of application No. 09/291,299, filed on Apr. 15, 1999, now Pat. No. 6,774,225.

(51) Int. Cl.
*A61K 39/00* (2006.01)
*A61K 38/00* (2006.01)
*C12P 21/06* (2006.01)

(52) U.S. Cl. ............................. 424/184.1; 424/185.1; 424/192.1; 530/806; 530/300; 435/69.1

(58) Field of Classification Search ...................... None
See application file for complete search history.

(56) References Cited

U.S. PATENT DOCUMENTS

| | | | |
|---|---|---|---|
| 4,743,554 | A | 5/1988 | Boothroyd et al. |
| 5,700,680 | A | 12/1997 | Newton et al. |
| 5,824,316 | A | 10/1998 | Grubman et al. |

FOREIGN PATENT DOCUMENTS

| | | |
|---|---|---|
| CN | 93112596.0 | 10/1993 |
| CN | 02137011.7 | 9/2002 |

OTHER PUBLICATIONS

Bona et al., "Immunogenicity of Microbial Peptides Grafted In Self Immunoglobin Molecules", Cellular and Molecular Biology, 40 (Suppl.1), 21-30, 1994.
Francis, "Peptide Vaccines: New Approaches To Immunopotentiation Vaccines: New-Generation Immunological Adjuvants", New York, 1995, 135-141.
Tam, "Synthetic Peptide Vaccine Design: Synthesis and Properties of a High-Density Multiple Antigenic Peptide System", Proc. Natl. Acad. Sci. USA, vol. 85,pp. 5409-5413, Aug. 1988.
Francis, "Enhanced Immuogenicity of Recombinant and Synthetic Peptide Vaccines", Vaccines, Edited by G. Gregoriadis et al., New York, 1991, pp. 13-23.
Broekhuijsen et al., Synthesis of Fusion Proteins With Multiple Copies of An Antigenic Determinant of Foot-And-Mouth Disease Virus, Medical Biological Laboratory TNO, 1986, pp. 189-197.
Winther et al., "Bacterially Expressed Anitgenic Peptide From Foot-And-Mouth Disease Virus Capsid Elicits Variable Immunologic Responses In Animals", Journal of Immunology, 1986, vol. 136, No. 5, pp. 1835-1840.
Krzych et al., "Repertoires of T Cells Directed Against A Large Protein Antigen", B Galactosidase, Journal of Immunology, vol. 126, No. 4, 1982, pp. 1529-1534.
Manca et al., "Constraints in T-B Cooperation Related to Epitope Topology On E. Coli B-Galactosidase", Journal of Immunology, 1985, 15, pp. 345-350.
Broekhuijsen et al., "Fusion Proteins with Multiple Copies of the Major Antigenic Determinant of Foot-And-Mouth Disease Virus Protect...", J. Gen Virol, 1987, 68, pp. 3137-3143.
Brumeanu, et al. "Engineering of doubly antigenized immunoglobulins expressing T and B viral epitopes," Immunotechnology 2:85-95 (1996).
Chan, et al. "An immunoglobulin G based chimeric protein induced foot-and-mouth disease specific immune response in swine" Vaccine 19:538-46 (2001).
Davis, H.L. "DNA Vaccines for Prophylactic or Therapeutic Immunization Against Hepatitis B Virus," The Mount Sanai Journal of Medicine 66:84-90 (1999).
DeNoon, D.J. "(AW) Conference Coverage (ISV): T-Cell VAccines Via Genetic, Enzymatic, Chemical Engineering," AIDSWEEKLY Plus, (1997).
Goodman, et al., "An immunological approach to the structural basis of the sweet taste," Pure & Appl. Chem. 69:715-9 (1997).
Hopp and Woods, "A computer program for predicting protein antigenic determinants," Mol. Immunol. 20:483-9 (1983).
Hopp and Woods, "Prediction of protein antigenic determinants from amino acid sequences," Proc. Natl. Sci. USA 78:3824-8 (1981).
Jones, et al. "Replacing the complementarity-determining regiouns in a human antibody with those from a mouse," Nature 321:522-5 (1986).
Klien (ed.), "Immunology" Blackwell Scientific Publishers, Massachusetts (1990) pp. 137, 139.
Lin and Zhang (ed.) "Modern Cellular & Molecular Immunology" Science Publications (2000) pp. 183-184.
Parry, et al. "Structural and serological evidence for a novel mechanism of antigenic variation in foot-and-mouth disease virus," Nature 347:569-72 (1990).
Riechmann, et al., "Reshaping human antibodies for therapy," Nature 332:323-7 (1988).

(Continued)

*Primary Examiner*—Zachariah Lucas
*Assistant Examiner*—Bo Peng
(74) *Attorney, Agent, or Firm*—Baker & McKenzie LLP

(57) ABSTRACT

Protein sequences encoding antigenized antibodies for treatment of foot-and-mouth disease (FMD) or foot-and-mouth disease virus (FMDV) of swine is provided. The antigenized antibodies are created from the grafting of peptide epitopes derived from FMDV into swine antibody CDR loops. FMDV peptide epitopes are cloned by PCR from VP1 gene of FMDV. The overlapping PCR method is used to insert the FMDV peptide epitopes into the CDR regions of swine immnuoglobulin heavy and light chains genes. The resulting antigenized antibody genes were cloned into mammalian expression vector. The plasmids are transfected into CHO or myeloma cells. The stable transfectant cell line was selected for high yield of the desired protein antibodies.

12 Claims, 17 Drawing Sheets

OTHER PUBLICATIONS

Wang (ed.) "Basic Molecular Immunology" Peking University Publications p. 22-3, date not available.

Xiong, et al. "Engineering vaccines with heterologous B and T cell epitopes using immunoglobulin genes," Nature Biotechechnology 15:882-6 (1997).

Zanetti, et al. "Expression of conformationally constrained adhesion peptide in an antibody CDR loop and inhibition of natural killer cell cytotoxic activity by an antibody antigenized with the RGD motif," EMBO Journal 12:4375-84 (1993).

Zanetti, et al. "Theoretical and Practical Aspects of Antigenized Antibodies," Immunological Review 130:125-50 (1992).

```
MEFRLNWVVL  FALLQGVQGE  EKLVESGGGL  VQPGGSLKLS  CVGSGFTFSS
TYIHWVRQAP  GKGLEWLAGL  YSSTTPTYYS  DSVKGRFDIS  REDAQNTAYL
QMNGLKTEDT  ARYYCGKRHK  QEIVAPVKQK  LWGPGVEVVV  SSAPKTAPSV
YPLAPCGRDV  SGPNVALGCL  ASSYFPEPVT  VTWNSGALTS  GVHTFPSVLQ
PSGLYSLSSM  VTVPASSLSS  KSYTCNVNHP  ATTTKVDKRV  GIHQPQTCPI
CPGCEVAGPS  VFIFPPKPKD  TLMISQTPEV  TCVVVDVSKE  HAEVQFSWYV
DGVEVHTAET  RPKEEQFNST  YRVVSVLPIQ  HQDWLKGKEF  KCKVNNVDLP
APITRTISKA  IGQSREPQVY  TLPPPAEELS  RSKVTLTCLV  IGFYPPDIHV
EWKSNGQPEP  ENTYRTTPPQ  QDVDGTFFLY  SKLAVDKARW  DHGDKFECAV
MHEALHNHYT  QKSISKTQGK
```

Figure 3

```
   1 ATGGAGTTTC GGCTGAACTG GGTGGTCTTG TTTGCTCTCT TACAAGGTGT CCAGGGTGAG
  61 GAGAAGCTGG TGGAGTCTGG AGGAGGCCTG GTGCAGCCTG GGGGGTCTCT GAAACTCTCC
 121 TGTGTCGGCT CTGGATTCAC CTTCAGTAGT ACCTATATTC ACTGGGTCCG CCAGGCTCCA
 181 GGGAAGGGAC TGGAGTGGCT GGCAGGTCTC TACAGTAGTA CTACGCCGAC CTACTACTCA
 241 GACTCTGTGA AGGGCCGGTT CGACATCTCC AGAGAGGACG CCCAGAACAC GGCCTATCTA
 301 CAAATGAACG GCCTGAAAAC CGAAGACACG GCCCGCTACT ACTGTGGAAA GCGTCACAAA
 361 CAGGAAATCG TAGCTCCAGT AAAACAGAAG TTGTGGGGCC CAGGCGTTGA AGTCGTCGTG
 421 TCCTCAGCCC CCAAGACGGC CCCATCGGTC TACCCTCTGG CCCCCTGCGG CAGGGACACG
 481 TCTGGCCCTA ACGTGGCCTT GGGCTGCCTG GCCTCAAGCT ACTTCCCCGA GCCAGTGACC
 541 ATGACCTGGA ACTCGGGCGC CCTGACCAGT GGCGTGCACA CCTTCCCATC CGTCCTGCAG
 601 CCGTCAGGGC TCTACTCCCT CAGCAGCATG GTGACCGTGC CGGCCAGCAG CCTGTCCAGC
 661 AAGAGCTACA CCTGCAATGT CAACCACCCG GCCACCACCA CCAAGGTGGA CAAGCGTGTT
 721 GGAATACACC AGCCGCAAAC ATGTCCCATA TGCCCAGGCT GTGAAGTGGC CGGGCCCTCG
 781 GTCTTCATCT TCCCTCCAAA ACCCAAGGAC ACCCTCATGA TCTCCCAGAC CCCCGAGGTC
 841 ACGTGCGTGG TGGTGGACGT CAGCAAGGAG CACGCCGAGG TCCAGTTCTC CTGGTACGTG
 901 GACGGGGTAG AGGTGCACAC GGCCGAGACG AGACCAAAGG AGGAGCAGTT CAACAGCACC
 961 TACCGTGTGG TCAGCGTCCT GCCCATCCAG CACCAGGACT GGCTGAAGGG GAAGGAGTTC
1021 AAGTGCAAGG TCAACAACGT AGACCTCCCA GCCCCCATCA CGAGGACCAT CTCCAAGGCT
1081 ATAGGGCAGA GCCGGGAGCC GCAGGTGTAC ACCCTGCCCC CACCCGCCGA GGAGCTGTCC
1141 AGGAGCAAAG TCACGCTAAC CTGCCTGGTC ATTGGCTTCT ACCCACCTGA CATCCATGTT
1201 GAGTGGAAGA GCAACGGACA GCCGGAGCCA GAGAACACAT ACCGCACCAC CCCGCCCCAG
1261 CAGGACGTGG ACGGGACCTT CTTCCTGTAC AGCAAACTCG CGGTGGACAA GGCAAGATGG
1321 GACCATGGAG ACAAATTTGA GTGTGCGGTG ATGCACGAGG CTCTGCACAA CCACTACACC
1381 CAGAAGTCCA TCTCCAAGAC TCAGGGTAAA TGA
```

Figure 4

```
MEFRLNWVVL FALLQGVQGE EKLVESGGGL VQPGGSLKLS CVGSGFTFSS
TYIHWVRQAP GKGLEWLAGL YSSTTPTYYS DSVKGRFDIS REDAQNTAYL
QMNGLKTEDT ARYYCGKVPN LRGDLQVLAQ KVARTLPWGP GVEVVVSSAP
KTAPSVYPLA PCGRDVSGPN VALGCLASSY FPEPVTVTWN SGALTSGVHT
FPSVLQPSGL YSLSSMVTVP ASSLSSKSYT CNVNHPATTT KVDKRVGIHQ
PQTCPICPGC EVAGPSVFIF PPKPKDTLMI SQTPEVTCVV VDVSKEHAEV
QFSWYVDGVE VHTAETRPKE EQFNSTYRVV SVLPIQHQDW LKGKEFKCKV
NNVDLPAPIT RTISKAIGQS REPQVYTLPP PAEELSRSKV TLTCLVIGFY
PPDIHVEWKS NGQPEPENTY RTTPPQQDVD GTFFLYSKLA VDKARWDHGD
KFECAVMHEA LHNHYTQKSI SKTQGK
```

Figure 5

```
   1 ATGGAGTTTC GGCTGAACTG GGTGGTCTTG TTTGCTCTCT TACAAGGTGT CCAGGGTGAG
  61 GAGAAGCTGG TGGAGTCTGG AGGAGGCCTG GTGCAGCCTG GGGGGTCTCT GAAACTCTCC
 121 TGTGTCGGCT CTGGATTCAC CTTCAGTAGT ACCTATATTC ACTGGGTCCG CCAGGCTCCA
 181 GGGAAGGGAC TGGAGTGGCT GGCAGGTCTC TACAGTAGTA CTACGCCGAC CTACTACTCA
 241 GACTCTGTGA AGGGCCGGTT CGACATCTCC AGAGAGGACG CCCAGAACAC GGCCTATCTA
 301 CAAATGAACG GCCTGAAAAC CGAAGACACG GCCCGCTACT ACTGTGGAAA GGTACCAAAC
 361 CTGCGTGGTG ACCTGCAGGT ACTTGCTCAG AAAGTTGCTC GTACTCTGCC ATGGGGCCCA
 421 GGCGTTGAAG TCGTCGTGTC CTCAGCCCCC AAGACGGCCC CATCGGTCTA CCCTCTGGCC
 481 CCCTGCGGCA GGGACACGTC TGGCCCTAAC GTGGCCTTGG GCTGCCTGGC CTCAAGCTAC
 541 TTCCCCGAGC CAGTGACCAT GACCTGGAAC TCGGGCGCCC TGACCAGTGG CGTGCACACC
 601 TTCCCATCCG TCCTGCAGCC GTCAGGGCTC TACTCCCTCA GCAGCATGGT GACCGTGCCG
 661 GCCAGCAGCC TGTCCAGCAA GAGCTACACC TGCAATGTCA ACCACCCGGC CACCACCACC
 721 AAGGTGGACA AGCGTGTTGG AATACACCAG CCGCAAACAT GTCCCATATG CCCAGGCTGT
 781 GAAGTGGCCG GGCCCTCGGT CTTCATCTTC CCTCCAAAAC CAAGGACAC CCTCATGATC
 841 TCCCAGACCC CCGAGGTCAC GTGCGTGGTG GTGGACGTCA GCAAGGAGCA CGCCGAGGTC
 901 CAGTTCTCCT GGTACGTGGA CGGGGTAGAG GTGCACACGG CCGAGACGAG ACCAAAGGAG
 961 GAGCAGTTCA ACAGCACCTA CCGTGTGGTC AGCGTCCTGC CATCCAGCA CCAGGACTGG
1021 CTGAAGGGGA AGGAGTTCAA GTGCAAGGTC AACAACGTAG ACCTCCCAGC CCCCATCACG
1081 AGGACCATCT CCAAGGCTAT AGGGCAGAGC CGGGAGCCGC AGGTGTACAC CCTGCCCCCA
1141 CCCGCCGAGG AGCTGTCCAG GAGCAAAGTC ACGCTAACCT GCCTGGTCAT GGCTTCTAC
1201 CCACCTGACA TCCATGTTGA GTGGAAGAGC AACGGACAGC CGGAGCCAGA GAACACATAC
1261 CGCACCACCC CGCCCCAGCA GGACGTGGAC GGGACCTTCT TCCTGTACAG CAAACTCGCG
1321 GTGGACAAGG CAAGATGGGA CCATGGAGAC AAATTTGAGT GTGCGGTGAT GCACGAGGCT
1381 CTGCACAACC ACTACACCCA GAAGTCCATC TCCAAGACTC AGGGTAAATG A
```

Figure 6

```
   1 GTACCAAACC TGCGTGGTGA CCTGCAGGTA CTTGCTCAGA AAGTTGCTCG TACTCTGCCA
  61 CGTCACAAAC AGGAAATCGT AGCTCCAGTA AAACAGAAGT TGGCCCCCAA GACGGCCCCA
 121 TCGGTCTACC CTCTGGCCCC CTGCGGCAGG GACGTGTCTG GCCCTAACGT GGCCTTGGGC
 181 TGCCTGGCCT CAAGCTACTT CCCCGAGCCA GTGACCGTGA CCTGGAACTC GGGCGCCCTG
 241 ACCAGTGGCG TGCACACCTT CCCATCCGTC CTGCAGCCGT CAGGGCTCTA CTCCCTCAGC
 301 AGCATGGTGA CCGTGCCGGC CAGCAGCCTG TCCAGCAAGA GCTACACCTG CAATGTCAAC
 361 CACCCGGCCA CCACCACCAA GGTGGACAAG CGTGTTGGAA TACACCAGCC GCAAACATGT
 421 CCCATATGCC CAGGCTGTGA AGTGGCCGGG CCCTCGGTCT TCATCTTCCC TCCAAAACCC
 481 AAGGACACCC TCATGATCTC CCAGACCCCC GAGGTCACGT GCGTGGTGGT GGACGTCAGC
 541 AAGGAGCACG CCGAGGTCCA GTTCTCCTGG TACGTGGACG GGGTAGAGGT GCACACGGCC
 601 GAGACGAGAC CAAAGGAGGA GCAGTTCAAC AGCACCTACC GTGTGGTCAG CGTCCTGCCC
 661 ATCCAGCACC AGGACTGGCT GAAGGGGAAG GAGTTCAAGT GCAAGGTCAA CAACGTAGAC
 721 CTCCCAGCCC CCATCACGAG GACCATCTCC AAGGCTATAG GGCAGAGCCG GGAGCCGCAG
 781 GTGTACACCC TGCCCCCACC CGCCGAGGAG CTGTCCAGGA GCAAAGTCAC GCTAACCTGC
 841 CTGGTCATTG GCTTCTACCC ACCTGACATC CATGTTGAGT GGAAGAGCAA CGGACAGCCG
 901 GAGCCAGAGA ACACATACCG CACCACCCCG CCCCAGCAGG ACGTGGACGG GACCTTCTTC
 961 CTGTACAGCA AACTCGCGGT GGACAAGGCA AGATGGGACC ATGGAGACAA ATTTGAGTGT
1021 GCGGTGATGC ACGAGGCTCT GCACAACCAC TACACCCAGA AGTCCATCTC CAAGACTCAG
1081 GGTAAATGA
```

Figure 7

VPNLRGDLQV LAQKVARTLP RHKQEIVAPV KQKLAPKTAP SVYPLAPCGR
DVSGPNVALG CLASSYFPEP VTVTWNSGAL TSGVHTFPSV LQPSGLYSLS
SMVTVPASSL SSKSYTCNVN HPATTTKVDK RVGIHQPQTC PICPGCEVAG
PSVFIFPPKP KDTLMISQTP EVTCVVVDVS KEHAEVQFSW YVDGVEVHTA
ETRPKEEQFN STYRVVSVLP IQHQDWLKGK EFKCKVNNVD LPAPITRTIS
KAIGQSREPQ VYTLPPPAEE LSRSKVTLTC LVIGFYPPDI HVEWKSNGQP
EPENTYRTTP PQQDVDGTFF LYSKLAVDKA RWDHGDKFEC AVMHEALHNH
YTQKSISKTQ GK

Figure 8

PIGL1 sequence

DSQTVIQKPA ISFSLGGTVT LTCAFSSGSL <u>TGINYPS</u>WFQ RTPGQPPQTV
IYN<u>TNNRPTG</u> VPIRFSGAIS GNKAALTITG AQAKDEADYF C<u>ALYKSSAQI</u>
<u>T</u>FGGGTHLTV LGQPKAAPTV NLFPPSSEEL GTNKATLVCL ISDFYPGAVT
VTWKAGGTTV TQGVETTKPS KQSNNKYAAS SYLALSASDW KSSSGFTCQV
THEGTIVEKT VTPSECA

PIGL2 sequence

DSQTVIQEPA MSVSPGGTVT LTCAFTSGSV <u>TTSNHPG</u>WYQ QTPGQPPRLV
IYR<u>TNNRPTG</u> VPSRFSGAIS GNKAALSITG AQANDEADYF C<u>TLWKDNTYF</u>
FGGGTRLTVL GQPKAAPMVN LFPPSSEELG TNKATLVCLI SDFYPGAVTV
TWKAGGTTVT QGVETTKPSK QSNNKYAASS YLALSASDWK SSSGFTCQVT
HEGTIVEKTV TPSECA

PIGL3 sequence

DSQTVIQEPA MSVSPGGTVT VTCAFSSGSV <u>TSSDYPS</u>WFQ QTPGQPPRTV
IYR<u>TNKPPDW</u> VPGLSGAMSG NKASLTITGA QAEDEADYFC <u>ALEEKSRYQV</u>
FGGGTHLTVL GQPKAAPTVN FFPPSSEELG TNKATLVCLI SDFYPGAVTV
TWKAGGTTVT QGVETTKPSK QSNNRYAASR YLALSASDWK FSSGFTCQVT
HEGTIVEKTV TPSECA

PIGL4 sequence

DSQTVIQEPA MSVSPGGTVA LTCAFSSGSV <u>TTSNYPS</u>WFQ TPGQPPRQLI
WR<u>TNNRPTGV</u> PGRFSGAISG NKAALTITGA QANDEADYFC <u>TLCKSTANVI</u>
FGGGTHLTVL GQPKAAPTVN LFPPSSEELG TNKATLVCLI SDFYPGAVTV
TWKAGGTTVT QGVETTKPSK QSNNRYAASR YLALSASDWK FSSGFTCQVT
HEGTIVEKTV TPSECA

Figure 9

A. PIGL1 Sequence
LOCUS PK
```
   1 GTGCCAAGGT TGCATGCCTG CAGGTCGACT AGTACGGGGG GGGGGGGGGG GGGCAGGAGG
  61 CTAAAGAGGC CCCTTCCCAA AATTGTCCCC ACCATGGCCT GAACGGTGCT TCTGATCGGG
 121 CTCCTCCCTG TCGGCTCAGG GGTGGATTCT CAAACTGTGA TCCAAAAACC GGCAATCTCT
 181 TTTTCTCTTG GAGGGACCGT CACACTCACC TGTGCCTTTA GCTCTGGGTC ACTCACTGGT
 241 ATTAACTACC CTAGCTGGTT CCAGCGGACA CCAGGCCAGC CTCCTCAAAC TGTTATCTAC
 301 AACACAAACA ACCGCCCGAC TGGGGTCCCC ATTCGCTTCT CTGGAGCCAT CTCTGGGAAC
 361 AAAGCCGCCC TCACCATCAC GGGGGCCCAG GCTAAGGACG AGGCCGACTA CTTCTGTGCT
 421 CTGTATAAAA GTAGCGCTCA GATTACGTTC GGCGGTGGGA CCCATCTGAC CGTCCTCGGT
 481 CAGCCCAAGG CCGCTCCCAC GGTCAACCTC TTCCCGCCCT CCTCTGAGGA GCTCGGCACC
 541 AACAAGGCCA CCCTGGTGTG TCTAATAAGT GACTTCTACC CGGGCGCCGT GACGGTGACC
 601 TGGAAGGCAG GCGGCACCAC CGTCACCCAG GGCGTGGAGA CCACCAAGCC CTCGAAACAG
 661 AGCAACAACA AGTACGCGGC CAGCAGCTAC CTGGCCCTGT CCGCCAGTGA CTGGAAATCT
 721 TCCAGCGGCT TCACCTGCCA GGTCACCCAC GAGGGGACCA TTGTGGAGAA GACAGTGACG
 781 CCCTCCGAGT GCGCC
```

Figure 10A

B. PIGL2 Sequence
LOCUS PKG
```
    1 GGGGGGGGGC TGAGGAGGCC GCGTCCCAAG ATTGTCCCCA CCATGGCCTG AACGGTGCTT
   61 CTGATCGGGC TCCTCGCTGT CGGCTCAGGG GTGGATTCTC AAACTGTGAT CCAGGAGCCG
  121 GCGATGTCAG TGTCTCCTGG AGGGACCGTC ACACTCACCT GTGCCTTTAC ATCTGGGTCA
  181 GTCACTACTA GTAACCACCC CGGCTGGTAC CAGCAGACAC CAGGCCAGCC TCCCCGACTG
  241 GTGATTTACA GGACAAACAA CCGCCCGACT GGGGTCCCCA GTCGCTTCTC TGGAGCCATC
  301 TCTGGGAACA AAGCCGCCCT CAGCATCACG GGGGCCCAGG CTAATGACGA GGCCGACTAT
  361 TTCTGTACTC TGTGGAAAGA TAACACATAT TTTTTCGGCG GTGGGACCCG TCTGACCGTC
  421 CTCGGTCAGC CCAAGGCCGC TCCCATGGTC AATCTCTTCC CGCCCTCCTC TGAGGAGCTC
  481 GGCACCAACA AGGCCACCCT GGTGTGTCTA ATAAGTGACT TCTACCCGGG CGCCGTGACG
  541 GTGACCTGGA AGGCAGGCGG CACCACCGTC ACCCAGGGCG TGGAGACCAC CAAGCCCTCG
  601 AAACAGAGCA ACAACAAGTA CGCGGCCAGC AGCTACCTGG CCCTGTCCGC CAGTGACTGG
  661 AAATCTTCCA GCGGCTTCAC CTGCCAGGTC ACCCACGAGG GGACCATTGT GGAGAAGACA
  721 GTGACGCCCT CCGAGTGCGC C
```

Figure 10B

```
C. PIGL3 Sequence
LOCUS PPL2
    1 GTGGATTCTC AGACTGTGAT CCAGGAGCCG GCGATGTCAG TGTCTCCTGG AGGGACCGTC
   61 ACAGTCACCT GTGCCTTTAG CTCTGGGTCA GTCACTAGTA GTGACTACCC AAGCTGGTTC
  121 CAGCAGACAC CAGGCCAGCC TCCTCGAACT GTCATCTACA GAACAAACAA GCCGCCCGAC
  181 TGGGTCCCAG GTCTCTCTGG AGCCATGTCT GGGAACAAAG CGTCCCTCAC CATCACGGGG
  241 GCCCAGGCTG AGGACGAGGC TGACTACTTC TGTGCTCTGG AGGAAAAGTC ACGGTATCAG
  301 GTTTTCGGCG GTGGGACCCA TTTGACCGTC CTCGGTCAGC CCAAGGCCGC TCCCACGGTC
  361 AACTTCTTCC CGCCCTCCTC TGAGGAGCTC GGCACCAACA AGGCCACCCT GGTGTGTCTA
  421 ATAAGTGACT TCTACCCGGG CGCCGTGACG GTGACCTGGA AGGCAGGCGG CACCACCGTC
  481 ACCCAGGGCG TGGAGACCAC CAAGCCCTCG AAACAGAGCA ACAACAGGTA CGCGGCCAGC
  541 AGGTACCTGG CCCTGTCCGC CAGTGACTGG AAATTCTCCA GCGGCTTCAC CTGCCAGGTC
  601 ACCCACGAGG GGACCATTGT GGAGAAGACA GTGACGCCCT CCGAGTGCGC C
```

Figure 10C

D. PIGL4 Sequence
LOCUS PPL4
```
   1 CCTGGACTCC TCTCTCCTGT TCGGGTGGAT TCTCAGACTG TGATCCAGGA GCCGGCGATG
  61 TCAGTGTCTC CTGGAGGGAC CGTCGCACTC ACCTGTGCCT TTAGCTCTGG GTCAGTCACT
 121 ACCAGTAACT ACCCCAGCTG GTTCCAGAAG ACACCAGGCC AGCCTCCCCG ACAGCTGATC
 181 TGGAGAACAA ACAACCGCCC GACTGGGGTC CCCGGTCGCT TCTCTGGAGC CATCTCTGGG
 241 AACAAAGCCG CCCTCACCAT CACGGGGGCC CAGGCTAATG ACGAGGCCGA CTACTTTTGT
 301 ACTCTGTGTA AAAGTACTGC TAATGTAATT TTCGGCGGTG GGACCCATCT GACCGTCCTC
 361 GGTCAGCCCA AGGCCGCTCC CACGGTCAAC CTCTTCCCGC CCTCCTCTGA GGAGCTCGGC
 421 ACCAACAAGG CCACCCTGGT GTGTCTAATA AGTGACTTCT ACCCGGGCGC CGTGACGGTG
 481 ACCTGGAAAG CAGGCGGCAC CACCGTCACC CAGGGCGTGG AGACAACCAA GCCCTCGAAA
 541 CAGAGCAACA ACAGGTACGC GGCCAGCAGG TACCTGGCCC TGTCCGCCAG TGACTGGAAA
 601 TTCTCCAGCG GCTTCACCTG CCAGGTCACC CACGAGGGGA CCATTGTGGA GAAGACAGTG
 661 ACGCCCTCCG AGTGCGCC
```

Figure 10D

SEQUENCE LISTING

<160> NUMBER OF SEQ ID NOS: 24

<210> SEQ ID NO 1
<211> LENGTH: 470
<212> TYPE: PRT
<213> ORGANISM: Sus sp.

<400> SEQUENCE: 1

```
Met Glu Phe Arg Leu Asn Trp Val Val Leu Phe Ala Leu Leu Gln Gly
1               5                   10                  15

Val Gln Gly Glu Glu Lys Leu Val Glu Ser Gly Gly Gly Leu Val Gln
            20                  25                  30

Pro Gly Gly Ser Leu Lys Leu Ser Cys Val Gly Ser Gly Phe Thr Phe
        35                  40                  45

Ser Ser Thr Tyr Ile His Trp Val Arg Gln Ala Pro Gly Lys Gly Leu
    50                  55                  60

Glu Trp Leu Ala Gly Leu Tyr Ser Ser Thr Thr Pro Thr Tyr Tyr Ser
65                  70                  75                  80

Asp Ser Val Lys Gly Arg Phe Asp Ile Ser Arg Glu Asp Ala Gln Asn
                85                  90                  95
```

Thr Ala Tyr Leu Gln Met Asn Gly Leu Lys Thr Glu Asp Thr Ala Arg
            100                 105                 110

Tyr Tyr Cys Gly Lys Arg His Lys Gln Glu Ile Val Ala Pro Val Lys
            115                 120                 125

Gln Lys Leu Trp Gly Pro Gly Val Glu Val Val Ser Ser Ala Pro
    130                 135                 140

Lys Thr Ala Pro Ser Val Tyr Pro Leu Ala Pro Cys Gly Arg Asp Val
145                 150                 155                 160

Ser Gly Pro Asn Val Ala Leu Gly Cys Leu Ala Ser Ser Tyr Phe Pro
                165                 170                 175

Glu Pro Val Thr Val Thr Trp Asn Ser Gly Ala Leu Thr Ser Gly Val
            180                 185                 190

His Thr Phe Pro Ser Val Leu Gln Pro Ser Gly Leu Tyr Ser Leu Ser
            195                 200                 205

Ser Met Val Thr Val Pro Ala Ser Ser Leu Ser Ser Lys Ser Tyr Thr
    210                 215                 220

Cys Asn Val Asn His Pro Ala Thr Thr Thr Lys Val Asp Lys Arg Val
225                 230                 235                 240

Gly Ile His Gln Pro Gln Thr Cys Pro Ile Cys Pro Gly Cys Glu Val
                245                 250                 255

Ala Gly Pro Ser Val Phe Ile Phe Pro Pro Lys Pro Lys Asp Thr Leu
            260                 265                 270

Met Ile Ser Gln Thr Pro Glu Val Thr Cys Val Val Val Asp Val Ser
            275                 280                 285

Lys Glu His Ala Glu Val Gln Phe Ser Trp Tyr Val Asp Gly Val Glu
    290                 295                 300

Val His Thr Ala Glu Thr Arg Pro Lys Glu Glu Gln Phe Asn Ser Thr
305                 310                 315                 320

Tyr Arg Val Val Ser Val Leu Pro Ile Gln His Gln Asp Trp Leu Lys
                325                 330                 335

Gly Lys Glu Phe Lys Cys Lys Val Asn Asn Val Asp Leu Pro Ala Pro
            340                 345                 350

Ile Thr Arg Thr Ile Ser Lys Ala Ile Gly Gln Ser Arg Glu Pro Gln
            355                 360                 365

Val Tyr Thr Leu Pro Pro Pro Ala Glu Glu Leu Ser Arg Ser Lys Val
    370                 375                 380

Thr Leu Thr Cys Leu Val Ile Gly Phe Tyr Pro Pro Asp Ile His Val
385                 390                 395                 400

Glu Trp Lys Ser Asn Gly Gln Pro Glu Pro Glu Asn Thr Tyr Arg Thr
                405                 410                 415

Thr Pro Pro Gln Gln Asp Val Asp Gly Thr Phe Phe Leu Tyr Ser Lys
            420                 425                 430

Leu Ala Val Asp Lys Ala Arg Trp Asp His Gly Asp Lys Phe Glu Cys
            435                 440                 445

Ala Val Met His Glu Ala Leu His Asn His Tyr Thr Gln Lys Ser Ile
    450                 455                 460

Ser Lys Thr Gln Gly Lys
465                 470

<210> SEQ ID NO 2
<211> LENGTH: 1413
<212> TYPE: DNA
<213> ORGANISM: Sus sp.

<400> SEQUENCE: 2

```
atggagtttc ggctgaactg ggtggtcttg tttgctctct tacaaggtgt ccagggtgag     60
gagaagctgg tggagtctgg aggaggcctg gtgcagcctg ggggtctct gaaactctcc    120
tgtgtcggct ctggattcac cttcagtagt acctatattc actgggtccg ccaggctcca   180
gggaagggac tggagtggct ggcaggtctc tacagtagta ctacgccgac ctactactca   240
gactctgtga agggccggtt cgacatctcc agagaggacg cccagaacac ggcctatcta   300
caaatgaacg gcctgaaaac cgaagacacg gcccgctact actgtggaaa gcgtcacaaa   360
caggaaatcg tagctccagt aaaacagaag ttgtggggcc aggcgttga agtcgtcgtg    420
tcctcagccc ccaagacggc ccatcggtc taccctctgg ccccctgcgg cagggacacg    480
tctggcccta acgtggcctt gggctgcctg gcctcaagct acttccccga gccagtgacc   540
atgacctgga actcgggcgc cctgaccagt ggcgtgcaca ccttcccatc cgtcctgcag   600
ccgtcagggc tctactccct cagcagcatg gtgaccgtgc cggccagcag cctgtccagc   660
aagagctaca cctgcaatgt caaccacccg ccaccacca ccaaggtgga caagcgtgtt    720
ggaatacacc agccgcaaac atgtcccata tgcccaggct gtgaagtggc cgggccctcg   780
gtcttcatct cccctccaaa acccaaggac accctcatga tctcccagac ccccgaggtc   840
acgtgcgtgg tggtggacgt cagcaaggag cacgccgagg tccagttctc ctggtacgtg   900
gacggggtag aggtgcacac ggccgagacg agaccaaagg aggagcagtt caacagcacc   960
taccgtgtgg tcagcgtcct gcccatccag caccaggact ggctgaaggg gaaggagttc  1020
aagtgcaagg tcaacaacgt agacctccca gcccccatca cgaggaccat ctccaaggct  1080
atagggcaga gccgggagcc gcaggtgtac accctgcccc cacccgccga ggagctgtcc  1140
aggagcaaag tcacgctaac ctgcctggtc attggcttct acccacctga catccatgtt  1200
gagtggaaga gcaacggaca gccggagcca gagaacacat accgcaccac cccgccccag  1260
caggacgtgg acgggacctt cttcctgtac agcaaactcg cggtggacaa ggcaagatgg  1320
gaccatggag acaaatttga gtgtgcggtg atgcacgagg ctctgcacaa ccactacacc  1380
cagaagtcca tctccaagac tcagggtaaa tga                                1413
```

<210> SEQ ID NO 3
<211> LENGTH: 476
<212> TYPE: PRT
<213> ORGANISM: Sus sp.

<400> SEQUENCE: 3

```
Met Glu Phe Arg Leu Asn Trp Val Val Leu Phe Ala Leu Leu Gln Gly
1               5                   10                  15

Val Gln Gly Glu Glu Lys Leu Val Glu Ser Gly Gly Gly Leu Val Gln
                20                  25                  30

Pro Gly Gly Ser Leu Lys Leu Ser Cys Val Gly Ser Gly Phe Thr Phe
            35                  40                  45

Ser Ser Thr Tyr Ile His Trp Val Arg Gln Ala Pro Gly Lys Gly Leu
        50                  55                  60

Glu Trp Leu Ala Gly Leu Tyr Ser Ser Thr Thr Pro Thr Tyr Tyr Ser
65                  70                  75                  80

Asp Ser Val Lys Gly Arg Phe Asp Ile Ser Arg Glu Asp Ala Gln Asn
                85                  90                  95

Thr Ala Tyr Leu Gln Met Asn Gly Leu Lys Thr Glu Asp Thr Ala Arg
            100                 105                 110
```

```
Tyr Tyr Cys Gly Lys Val Pro Asn Leu Arg Gly Asp Leu Gln Val Leu
        115                 120                 125

Ala Gln Lys Val Ala Arg Thr Leu Pro Trp Gly Pro Gly Val Glu Val
130                 135                 140

Val Val Ser Ser Ala Pro Lys Thr Ala Pro Ser Val Tyr Pro Leu Ala
145                 150                 155                 160

Pro Cys Gly Arg Asp Val Ser Gly Pro Asn Val Ala Leu Gly Cys Leu
                165                 170                 175

Ala Ser Ser Tyr Phe Pro Glu Pro Val Thr Val Thr Trp Asn Ser Gly
            180                 185                 190

Ala Leu Thr Ser Gly Val His Thr Phe Pro Ser Val Leu Gln Pro Ser
        195                 200                 205

Gly Leu Tyr Ser Leu Ser Ser Met Val Thr Val Pro Ala Ser Ser Leu
    210                 215                 220

Ser Ser Lys Ser Tyr Thr Cys Asn Val Asn His Pro Ala Thr Thr Thr
225                 230                 235                 240

Lys Val Asp Lys Arg Val Gly Ile His Gln Pro Gln Thr Cys Pro Ile
                245                 250                 255

Cys Pro Gly Cys Glu Val Ala Gly Pro Ser Val Phe Ile Phe Pro Pro
            260                 265                 270

Lys Pro Lys Asp Thr Leu Met Ile Ser Gln Thr Pro Glu Val Thr Cys
        275                 280                 285

Val Val Val Asp Val Ser Lys Glu His Ala Glu Val Gln Phe Ser Trp
    290                 295                 300

Tyr Val Asp Gly Val Glu Val His Thr Ala Glu Thr Arg Pro Lys Glu
305                 310                 315                 320

Glu Gln Phe Asn Ser Thr Tyr Arg Val Val Ser Val Leu Pro Ile Gln
                325                 330                 335

His Gln Asp Trp Leu Lys Gly Lys Glu Phe Lys Cys Lys Val Asn Asn
            340                 345                 350

Val Asp Leu Pro Ala Pro Ile Thr Arg Thr Ile Ser Lys Ala Ile Gly
        355                 360                 365

Gln Ser Arg Glu Pro Gln Val Tyr Thr Leu Pro Pro Ala Glu Glu
    370                 375                 380

Leu Ser Arg Ser Lys Val Thr Leu Thr Cys Leu Val Ile Gly Phe Tyr
385                 390                 395                 400

Pro Pro Asp Ile His Val Glu Trp Lys Ser Asn Gly Gln Pro Glu Pro
                405                 410                 415

Glu Asn Thr Tyr Arg Thr Thr Pro Pro Gln Gln Asp Val Asp Gly Thr
            420                 425                 430

Phe Phe Leu Tyr Ser Lys Leu Ala Val Asp Lys Ala Arg Trp Asp His
        435                 440                 445

Gly Asp Lys Phe Glu Cys Ala Val Met His Glu Ala Leu His Asn His
    450                 455                 460

Tyr Thr Gln Lys Ser Ile Ser Lys Thr Gln Gly Lys
465                 470                 475

<210> SEQ ID NO 4
<211> LENGTH: 1431
<212> TYPE: DNA
<213> ORGANISM: Sus sp.

<400> SEQUENCE: 4
atggagtttc ggctgaactg ggtggtcttg tttgctctct tacaaggtgt ccagggtgag    60
```

-continued

```
gagaagctgg tggagtctgg aggaggcctg gtgcagcctg gggggtctct gaaactctcc      120
tgtgtcggct ctggattcac cttcagtagt acctatattc actgggtccg ccaggctcca      180
gggaagggac tggagtggct ggcaggtctc tacagtagta ctacgccgac ctactactca      240
gactctgtga agggccggtt cgacatctcc agagaggacg cccagaacac ggcctatcta      300
caaatgaacg gcctgaaaac cgaagacacg gcccgctact actgtggaaa ggtaccaaac      360
ctgcgtggtg acctgcaggt acttgctcag aaagttgctc gtactctgcc atggggccca      420
ggcgttgaag tcgtcgtgtc ctcagccccc aagacggccc catcggtcta ccctctggcc      480
ccctgcggca gggacacgtc tggccctaac gtggccttgg gctgcctggc tcaagctac       540
ttccccgagc cagtgaccat gacctggaac tcgggcgccc tgaccagtgg cgtgcacacc      600
ttcccatccg tcctgcagcc gtcagggctc tactccctca gcagcatggt gaccgtgccg      660
gccagcagcc tgtccagcaa gagctacacc tgcaatgtca accaccggc caccaccacc       720
aaggtggaca gcgtgttgg aatacaccag ccgcaaacat gtcccatatg cccaggctgt       780
gaagtggccg ggccctcggt cttcatcttc cctccaaaac ccaaggacac cctcatgatc      840
tcccagaccc ccgaggtcac gtgcgtggtg gtggacgtca gcaaggagca cgccgaggtc      900
cagttctcct ggtacgtgga cggggtagag gtgcacacgg ccgagacgag accaaaggag      960
gagcagttca acagcaccta ccgtgtggtc agcgtcctgc ccatccagca ccaggactgg     1020
ctgaagggga aggagttcaa gtgcaaggtc aacaacgtag acctcccagc ccccatcacg     1080
aggaccatct ccaaggctat agggcagagc cgggagccgc agtgtacac cctgcccccca     1140
cccgccgagg agctgtccag gagcaaagtc acgctaacct gcctggtcat tggcttctac     1200
ccacctgaca tccatgttga gtggaagagc aacggacagc cggagccaga gaacacatac     1260
cgcaccaccc cgccccagca ggacgtggac gggaccttct tcctgtacag caaactcgcg     1320
gtggacaagg caagatggga ccatggagac aaatttgagt gtgcggtgat gcacgaggct     1380
ctgcacaacc actacaccca gaagtccatc tccaagactc agggtaaatg a              1431
```

<210> SEQ ID NO 5
<211> LENGTH: 362
<212> TYPE: PRT
<213> ORGANISM: Sus sp.

<400> SEQUENCE: 5

```
Val Pro Asn Leu Arg Gly Asp Leu Gln Val Leu Ala Gln Lys Val Ala
1               5                   10                  15

Arg Thr Leu Pro Arg His Lys Gln Glu Ile Val Ala Pro Val Lys Gln
            20                  25                  30

Lys Leu Ala Pro Lys Thr Ala Pro Ser Val Tyr Pro Leu Ala Pro Cys
        35                  40                  45

Gly Arg Asp Val Ser Gly Pro Asn Val Ala Leu Gly Cys Leu Ala Ser
    50                  55                  60

Ser Tyr Phe Pro Glu Pro Val Thr Val Thr Trp Asn Ser Gly Ala Leu
65                  70                  75                  80

Thr Ser Gly Val His Thr Phe Pro Ser Val Leu Gln Pro Ser Gly Leu
                85                  90                  95

Tyr Ser Leu Ser Ser Met Val Thr Val Pro Ala Ser Ser Leu Ser Ser
            100                 105                 110

Lys Ser Tyr Thr Cys Asn Val Asn His Pro Ala Thr Thr Thr Lys Val
        115                 120                 125

Asp Lys Arg Val Gly Ile His Gln Pro Gln Thr Cys Pro Ile Cys Pro
```

```
            130                 135                 140
Gly Cys Glu Val Ala Gly Pro Ser Val Phe Ile Phe Pro Pro Lys Pro
145                 150                 155                 160

Lys Asp Thr Leu Met Ile Ser Gln Thr Pro Glu Val Thr Cys Val Val
                165                 170                 175

Val Asp Val Ser Lys Glu His Ala Glu Val Gln Phe Ser Trp Tyr Val
                180                 185                 190

Asp Gly Val Glu Val His Thr Ala Glu Thr Arg Pro Lys Glu Glu Gln
                195                 200                 205

Phe Asn Ser Thr Tyr Arg Val Val Ser Val Leu Pro Ile Gln His Gln
210                 215                 220

Asp Trp Leu Lys Gly Lys Glu Phe Lys Cys Lys Val Asn Asn Val Asp
225                 230                 235                 240

Leu Pro Ala Pro Ile Thr Arg Thr Ile Ser Lys Ala Ile Gly Gln Ser
                245                 250                 255

Arg Glu Pro Gln Val Tyr Thr Leu Pro Pro Pro Ala Glu Glu Leu Ser
                260                 265                 270

Arg Ser Lys Val Thr Leu Thr Cys Leu Val Ile Gly Phe Tyr Pro Pro
                275                 280                 285

Asp Ile His Val Glu Trp Lys Ser Asn Gly Gln Pro Glu Pro Glu Asn
                290                 295                 300

Thr Tyr Arg Thr Thr Pro Pro Gln Gln Asp Val Asp Gly Thr Phe Phe
305                 310                 315                 320

Leu Tyr Ser Lys Leu Ala Val Asp Lys Ala Arg Trp Asp His Gly Asp
                325                 330                 335

Lys Phe Glu Cys Ala Val Met His Glu Ala Leu His Asn His Tyr Thr
                340                 345                 350

Gln Lys Ser Ile Ser Lys Thr Gln Gly Lys
                355                 360

<210> SEQ ID NO 6
<211> LENGTH: 1089
<212> TYPE: DNA
<213> ORGANISM: Sus sp.

<400> SEQUENCE: 6
gtaccaaacc tgcgtggtga cctgcaggta cttgctcaga aagttgctcg tactctgcca      60
cgtcacaaac aggaaatcgt agctccagta aaacagaagt tggcccccaa gacggcccca     120
tcggtctacc ctctggcccc ctgcggcagg gacgtgtctg ccctaacgt ggccttgggc      180 tgcctggcct caagctactt ccccgagcca gtgaccgtga cctggaactc gggcgccctg     240
accagtggcg tgcacacctt cccatccgtc ctgcagccgt cagggctcta ctccctcagc     300
agcatggtga ccgtgccggc cagcagcctg tccagcaaga gctacacctg caatgtcaac     360
cacccggcca ccaccaccaa ggtggacaag cgtgttggaa tacaccagcc gcaaacatgt     420
cccatatgcc aggctgtgca gtggccgggc cctcggtctt catcttccc tccaaaaccc      480 aaggacaccc tcatgatctc ccagacccc gaggtcacgt gcgtggtggt ggacgtcagc     540
aaggagcacg ccgaggtcca gttctcctgg tacgtggacg gggtagaggt gcacacggcc     600
gagacgagac caaaggagga gcagttcaac agcacctacc gtgtggtcag cgtcctgccc     660
atccagcacc aggactggct gaaggggaag gagttcaagt gcaaggtcaa caacgtagac     720
ctcccagccc ccatcacgag gaccatctcc aaggctatag gcagagccg ggagccgcag      780 gtgtacaccc tgccccacc cgccgaggag ctgtccagga gcaaagtcac gctaacctgc     840
```

```
ctggtcattg gcttctaccc acctgacatc catgttgagt ggaagagcaa cggacagccg      900
gagccagaga acacataccg caccacccg ccccagcagg acgtggacgg gaccttcttc       960
ctgtacagca aactcgcggt ggacaaggca agatgggacc atggagacaa atttgagtgt    1020
gcggtgatgc acgaggctct gcacaaccac tacacccaga agtccatctc caagactcag    1080
ggtaaatga                                                             1089
```

<210> SEQ ID NO 7
<211> LENGTH: 217
<212> TYPE: PRT
<213> ORGANISM: Sus sp.

<400> SEQUENCE: 7

```
Asp Ser Gln Thr Val Ile Gln Lys Pro Ala Ile Ser Phe Ser Leu Gly
1               5                   10                  15

Gly Thr Val Thr Leu Thr Cys Ala Phe Ser Gly Ser Leu Thr Gly
            20                  25                  30

Ile Asn Tyr Pro Ser Trp Phe Gln Arg Thr Pro Gly Gln Pro Pro Gln
        35                  40                  45

Thr Val Ile Tyr Asn Thr Asn Asn Arg Pro Thr Gly Val Pro Ile Arg
    50                  55                  60

Phe Ser Gly Ala Ile Ser Gly Asn Lys Ala Ala Leu Thr Ile Thr Gly
65                  70                  75                  80

Ala Gln Ala Lys Asp Glu Ala Asp Tyr Phe Cys Ala Leu Tyr Lys Ser
                85                  90                  95

Ser Ala Gln Ile Thr Phe Gly Gly Gly Thr His Leu Thr Val Leu Gly
            100                 105                 110

Gln Pro Lys Ala Ala Pro Thr Val Asn Leu Phe Pro Pro Ser Ser Glu
        115                 120                 125

Glu Leu Gly Thr Asn Lys Ala Thr Leu Val Cys Leu Ile Ser Asp Phe
    130                 135                 140

Tyr Pro Gly Ala Val Thr Val Thr Trp Lys Ala Gly Gly Thr Thr Val
145                 150                 155                 160

Thr Gln Gly Val Glu Thr Thr Lys Pro Ser Lys Gln Ser Asn Asn Lys
                165                 170                 175

Tyr Ala Ala Ser Ser Tyr Leu Ala Leu Ser Ala Ser Asp Trp Lys Ser
            180                 185                 190

Ser Ser Gly Phe Thr Cys Gln Val Thr His Glu Gly Thr Ile Val Glu
        195                 200                 205

Lys Thr Val Thr Pro Ser Glu Cys Ala
    210                 215
```

<210> SEQ ID NO 8
<211> LENGTH: 795
<212> TYPE: DNA
<213> ORGANISM: Sus sp.

<400> SEQUENCE: 8

```
gtgccaaggt tgcatgcctg caggtcgact agtacggggg ggggggggg gggcaggagg       60 ctaaagaggc cccttcccaa aattgtcccc accatggcct gaacggtgct tctgatcggg    120
ctcctccctg tcggctcagg ggtggattct caaactgtga tccaaaaacc ggcaatctct    180
ttttctcttg gagggaccgt cacactcacc tgtgccttta gctctgggtc actcactggt    240
attaactacc ctagctggtt ccagcggaca ccaggccagc ctcctcaaac tgttatctac    300
```

```
aacacaaaca accgcccgac tgggtcccc attcgcttct ctggagccat ctctgggaac      360
aaagccgccc tcaccatcac ggggcccag gctaaggacg aggccgacta cttctgtgct      420
ctgtataaaa gtagcgctca gattacgttc ggcggtggga cccatctgac cgtcctcggt     480
cagcccaagg ccgctcccac ggtcaacctc ttcccgccct cctctgagga gctcggcacc    540
aacaaggcca ccctggtgtg tctaataagt gacttctacc cgggcgccgt gacggtgacc    600
tggaaggcag gcggcaccac cgtcacccag ggcgtggaga ccaccaagcc ctcgaaacag    660
agcaacaaca agtacgcggc cagcagctac ctggccctgt ccgccagtga ctggaaatct    720
tccagcggct tcacctgcca ggtcacccac gaggggacca ttgtggagaa gacagtgacg   780
ccctccgagt gcgcc                                                       795

<210> SEQ ID NO 9
<211> LENGTH: 216
<212> TYPE: PRT
<213> ORGANISM: Sus sp.

<400> SEQUENCE: 9

Asp Ser Gln Thr Val Ile Gln Glu Pro Ala Met Ser Val Ser Pro Gly
1               5                  10                  15

Gly Thr Val Thr Leu Thr Cys Ala Phe Thr Ser Gly Ser Val Thr Thr
            20                  25                  30

Ser Asn His Pro Gly Trp Tyr Gln Gln Thr Pro Gly Gln Pro Pro Arg
        35                  40                  45

Leu Val Ile Tyr Arg Thr Asn Asn Arg Pro Thr Gly Val Pro Ser Arg
    50                  55                  60

Phe Ser Gly Ala Ile Ser Gly Asn Lys Ala Ala Leu Ser Ile Thr Gly
65                  70                  75                  80

Ala Gln Ala Asn Asp Glu Ala Asp Tyr Phe Cys Thr Leu Trp Lys Asp
                85                  90                  95

Asn Thr Tyr Phe Phe Gly Gly Gly Thr Arg Leu Thr Val Leu Gly Gln
            100                 105                 110

Pro Lys Ala Ala Pro Met Val Asn Leu Phe Pro Pro Ser Ser Glu Glu
        115                 120                 125

Leu Gly Thr Asn Lys Ala Thr Leu Val Cys Leu Ile Ser Asp Phe Tyr
    130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Lys Tyr
                165                 170                 175

Ala Ala Ser Ser Tyr Leu Ala Leu Ser Ala Ser Asp Trp Lys Ser Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
    210                 215

<210> SEQ ID NO 10
<211> LENGTH: 741
<212> TYPE: DNA
<213> ORGANISM: Sus sp.

<400> SEQUENCE: 10
gggggggggc tgaggaggcc gcgtcccaag attgtcccca ccatggcctg aacggtgctt     60
ctgatcgggc tcctcgctgt cggctcaggg gtggattctc aaactgtgat ccaggagccg    120
```

```
gcgatgtcag tgtctcctgg agggaccgtc acactcacct gtgcctttac atctgggtca      180
gtcactacta gtaaccaccc cggctggtac cagcagacac caggccagcc tccccgactg      240
gtgatttaca ggacaaacaa ccgcccgact ggggtcccca gtcgcttctc tggagccatc      300
tctgggaaca aagccgccct cagcatcacg ggggcccagg ctaatgacga ggccgactat      360
ttctgtactc tgtggaaaga taacacatat tttttcggcg gtgggacccg tctgaccgtc      420
ctcggtcagc ccaaggccgc tcccatggtc aatctcttcc cgccctcctc tgaggagctc      480
ggcaccaaca aggccaccct ggtgtgtcta ataagtgact ctacccgggg cgccgtgacg      540
gtgacctgga aggcaggcgg caccaccgtc acccagggcg tggagaccac caagccctcg      600
aaacagagca caacaagta cgcggccagc agctacctgg ccctgtccgc cagtgactgg      660
aaatcttcca gcggcttcac ctgccaggtc acccacgagg ggaccattgt ggagaagaca      720
gtgacgccct ccgagtgcgc c                                                741
```

```
<210> SEQ ID NO 11
<211> LENGTH: 216
<212> TYPE: PRT
<213> ORGANISM: Sus sp.

<400> SEQUENCE: 11

Asp Ser Gln Thr Val Ile Gln Glu Pro Ala Met Ser Val Ser Pro Gly
1               5                   10                  15

Gly Thr Val Thr Val Thr Cys Ala Phe Ser Ser Gly Ser Val Thr Ser
            20                  25                  30

Ser Asp Tyr Pro Ser Trp Phe Gln Gln Thr Pro Gly Gln Pro Pro Arg
        35                  40                  45

Thr Val Ile Tyr Arg Thr Asn Lys Pro Pro Asp Trp Val Pro Gly Leu
    50                  55                  60

Ser Gly Ala Met Ser Gly Asn Lys Ala Ser Leu Thr Ile Thr Gly Ala
65                  70                  75                  80

Gln Ala Glu Asp Glu Ala Asp Tyr Phe Cys Ala Leu Glu Glu Lys Ser
                85                  90                  95

Arg Tyr Gln Val Phe Gly Gly Gly Thr His Leu Thr Val Leu Gly Gln
            100                 105                 110

Pro Lys Ala Ala Pro Thr Val Asn Phe Pro Pro Ser Ser Glu Glu
        115                 120                 125

Leu Gly Thr Asn Lys Ala Thr Leu Val Cys Leu Ile Ser Asp Phe Tyr
    130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Arg Tyr
                165                 170                 175

Ala Ala Ser Arg Tyr Leu Ala Leu Ser Ala Ser Asp Trp Lys Phe Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
    210                 215

<210> SEQ ID NO 12
<211> LENGTH: 651
<212> TYPE: DNA
<213> ORGANISM: Sus sp.
```

-continued

<400> SEQUENCE: 12

```
gtggattctc agactgtgat ccaggagccg gcgatgtcag tgtctcctgg agggaccgtc    60
acagtcacct gtgcctttag ctctgggtca gtcactagta gtgactaccc aagctggttc   120
cagcagacac caggccagcc tcctcgaact gtcatctaca gaacaaacaa gccgcccgac   180
tgggtcccag gtctctctgg agccatgtct gggaacaaag cgtccctcac catcacgggg   240
gcccaggctg aggacgaggc tgactacttc tgtgctctgg aggaaaagtc acggtatcag   300
gttttcggcg gtgggaccca tttgaccgtc ctcggtcagc ccaaggccgc tcccacggtc   360
aacttcttcc cgccctcctc tgaggagctc ggcaccaaca aggccaccct ggtgtgtcta   420
ataagtgact tctacccggg cgccgtgacg gtgacctgga aggcaggcgg caccaccgtc   480
acccagggcg tggagaccac caagccctcg aaacagagca caacaggta cgcggccagc   540 aggtacctgg ccctgtccgc cagtgactgg aaattctcca gcggcttcac ctgccaggtc   600
acccacgagg ggaccattgt ggagaagaca gtgacgccct ccgagtgcgc c           651
```

<210> SEQ ID NO 13
<211> LENGTH: 216
<212> TYPE: PRT
<213> ORGANISM: Sus sp.

<400> SEQUENCE: 13

```
Asp Ser Gln Thr Val Ile Gln Glu Pro Ala Met Ser Val Ser Pro Gly
1               5                   10                  15

Gly Thr Val Ala Leu Thr Cys Ala Phe Ser Ser Gly Ser Val Thr Thr
            20                  25                  30

Ser Asn Tyr Pro Ser Trp Phe Gln Thr Pro Gly Gln Pro Pro Arg Gln
        35                  40                  45

Leu Ile Trp Arg Thr Asn Asn Arg Pro Thr Gly Val Pro Gly Arg Phe
    50                  55                  60

Ser Gly Ala Ile Ser Gly Asn Lys Ala Ala Leu Thr Ile Thr Gly Ala
65                  70                  75                  80

Gln Ala Asn Asp Glu Ala Asp Tyr Phe Cys Thr Leu Cys Lys Ser Thr
                85                  90                  95

Ala Asn Val Ile Phe Gly Gly Gly Thr His Leu Thr Val Leu Gly Gln
            100                 105                 110

Pro Lys Ala Ala Pro Thr Val Asn Leu Phe Pro Pro Ser Ser Glu Glu
        115                 120                 125

Leu Gly Thr Asn Lys Ala Thr Leu Val Cys Leu Ile Ser Asp Phe Tyr
    130                 135                 140

Pro Gly Ala Val Thr Val Thr Trp Lys Ala Gly Gly Thr Thr Val Thr
145                 150                 155                 160

Gln Gly Val Glu Thr Thr Lys Pro Ser Lys Gln Ser Asn Asn Arg Tyr
                165                 170                 175

Ala Ala Ser Arg Tyr Leu Ala Leu Ser Ala Ser Asp Trp Lys Phe Ser
            180                 185                 190

Ser Gly Phe Thr Cys Gln Val Thr His Glu Gly Thr Ile Val Glu Lys
        195                 200                 205

Thr Val Thr Pro Ser Glu Cys Ala
    210                 215
```

<210> SEQ ID NO 14
<211> LENGTH: 678
<212> TYPE: DNA
<213> ORGANISM: Sus sp.

<400> SEQUENCE: 14

```
cctggactcc tctctcctgt tcgggtggat tctcagactg tgatccagga gccggcgatg      60
tcagtgtctc ctggagggac cgtcgcactc acctgtgcct ttagctctgg gtcagtcact     120
accagtaact accccagctg gttccagaag acaccaggcc agcctccccg acagctgatc     180
tggagaacaa caaccgcccc gactggggtc cccggtcgct tctctggagc catctctggg     240
aacaaagccg ccctcaccat cacgggggcc caggctaatg acgaggccga ctacttttgt     300
actctgtgta aaagtactgc taatgtaatt ttcggcggtg ggaccatctc gaccgtcctc     360
ggtcagccca aggccgctcc cacggtcaac ctcttcccgc cctcctctga ggagctcggc     420
accaacaagg ccaccctggt gtgtctaata agtgacttct accgggcgc cgtgacggtg      480
acctggaaag caggcggcac caccgtcacc cagggcgtgg agacaaccaa gccctcgaaa     540
cagagcaaca caggtacgc ggccagcagg tacctggccc tgtccgccag tgactggaaa      600
ttctccagcg gcttcacctg ccaggtcacc cacgagggga ccattgtgga agacagtg      660
acgccctccg agtgcgcc                                                  678
```

<210> SEQ ID NO 15
<211> LENGTH: 28
<212> TYPE: DNA
<213> ORGANISM: Artificial
<220> FEATURE:
<223> OTHER INFORMATION: Primer

<400> SEQUENCE: 15

```
gacgctcgag tcatcattta ccctgagt                                        28
```

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16

```
agctaagctt gcccccaaga cggcccca                                        28
```

<210> SEQ ID NO 17
<211> LENGTH: 19
<212> TYPE: DNA
<213> ORGANISM: Artificial
<220> FEATURE:
<223> OTHER INFORMATION: Primer

<400> SEQUENCE: 17

```
atgccatatg gtaccaaac                                                  19
```

<210> SEQ ID NO 18
<211> LENGTH: 19
<212> TYPE: DNA
<213> ORGANISM: Artificial
<220> FEATURE:
<223> OTHER INFORMATION: Primer

<400> SEQUENCE: 18

```
atgcaagctt caacttctg                                                  19
```

<210> SEQ ID NO 19
<211> LENGTH: 14
<212> TYPE: PRT

<213> ORGANISM: Artificial
<220> FEATURE:
<223> OTHER INFORMATION: Epitope

<400> SEQUENCE: 19

Arg His Lys Gln Glu Ile Val Ala Pro Val Lys Gln Lys Leu
1               5                   10

<210> SEQ ID NO 20
<211> LENGTH: 42
<212> TYPE: DNA
<213> ORGANISM: Artificial
<220> FEATURE:
<223> OTHER INFORMATION: Epitope

<400> SEQUENCE: 20
cgtcacaaac aggaaatcgt agctccagta aaacagaagt tg                          42

<210> SEQ ID NO 21
<211> LENGTH: 20
<212> TYPE: PRT
<213> ORGANISM: Artificial
<220> FEATURE:
<223> OTHER INFORMATION: Epitope

<400> SEQUENCE: 21

Val Pro Asn Leu Arg Gly Asp Leu Gln Val Leu Ala Gln Lys Val Ala
1               5                   10                  15

Arg Thr Leu Pro
            20

<210> SEQ ID NO 22
<211> LENGTH: 60
<212> TYPE: DNA
<213> ORGANISM: Artificial
<220> FEATURE:
<223> OTHER INFORMATION: Epitope

<400> SEQUENCE: 22
gtaccaaacc tgcgtggtga cctgcaggta cttgctcaga aagttgctcg tactctgcca      60

<210> SEQ ID NO 23
<211> LENGTH: 34
<212> TYPE: PRT
<213> ORGANISM: Artificial
<220> FEATURE:
<223> OTHER INFORMATION: Epitope

<400> SEQUENCE: 23

Val Pro Asn Leu Arg Gly Asp Leu Gln Val Leu Ala Gln Lys Val Ala
1               5                   10                  15

Arg Thr Leu Pro Arg His Lys Gln Glu Ile Val Ala Pro Val Lys Gln
            20                  25                  30

Lys Leu

<210> SEQ ID NO 24
<211> LENGTH: 102
<212> TYPE: DNA
<213> ORGANISM: Artificial

```
<220> FEATURE:
<223> OTHER INFORMATION: Epitope

<400> SEQUENCE: 24
gtaccaaacc tgcgtggtga cctgcaggta cttgctcaga aagttgctcg tactctgcca        60
cgtcacaaac aggaaatcgt agctccagta aaacagaagt tg                         102
```

PROTEIN SEQUENCES CONTAINING ANTIGENIZED ANTIBODIES FOR FOOT-AND-MOUTH DISEASE

RELATED APPLICATIONS AND PRIORITY CLAIM

This is a continuation of U.S. application Ser. No. 09/291,299 filed Apr. 15, 1999, now issued as U.S. Pat. No. 6,774,225, entitled "Antigenized Antibody Vaccine For Foot-And-Mouth Disease" incorporated herein by reference.

BACKGROUND

1. Field

The present invention relates to protein sequences encoding antigenized swine antibodies for Foot-and-Mouth Disease (FMD), Foot-and-Mouth Disease Virus (FMDV), or their epitopes.

2. Background

Antibodies are proteins produced by the body's immune system in response to foreign elements known as antigens, which invade the body. Antibodies can elicit an immune response, which subsequently protects the host from infection by the disease-causing agents (antigens).

Foot-and-Mouth Disease, also known as FMD hereinafter, is a highly contagious, severely debilitating disease that infects all cloven-hoofed animals. It is endemic in many developing countries worldwide. In particular, swine in Asia have often been affected by FMD. FMD reduces livestock, productivity, incurs high vaccination costs, and restricts the international trade of livestock and livestock products. FMD is a viral infectious disease and the foot-and-mouth disease virus, also known as FMDV hereinafter, is a small animal virus having a single stranded positive sense RNA genome of about 8,000 nucleotides.

Two major types of vaccines have been produced against FMD. They are conventional vaccines and synthetic peptide vaccines. Conventional vaccines against FMDV use either inactivated FMD virus or a live attenuated FMD virus. The conventional vaccine approach, although generally effective, have several undesirable drawbacks associated with it.

Firstly, it is cost inefficient. This type of vaccine is made from large amounts of live, infectious virus. Maintaining and processing a large quantity of infectious virus is expensive, labor intensive and space inefficient.

Second and most importantly, these vaccines are potentially dangerous. Most of the outbreaks of FMD in recent years have been caused either by the escape of virus from vaccine production units or the use of incompletely inactivated or insufficiently attenuated virus. For example, during the 1980's, a number of outbreaks occurred in European countries including Italy, United Kingdom, France and in Taiwan in 1996. As the causative viruses of outbreaks were often found to be closely related or even identical to the strains that were used in Europe for manufacturing, it is possible that the primary outbreaks were caused by inadequately inactivated vaccines or by virus that escaped from vaccine production plants.

Another problem associated with producing conventional vaccine is that they are thermolabile. Conventional FMD vaccines are relatively unstable when exposed to elevated temperatures and they have to be stored at low temperatures. Constantly maintaining the required low temperatures is often not easily achievable, especially in tropical countries.

An addition potential problem in a virus culturing procedure of the conventional vaccine production vaccine production process is the use of fetal bovine serum virus culturing. It is possible that diseases can be introduced from the fetal bovine serum and affect the vaccinated animals.

Yet another major disadvantage of using conventional FMD vaccines is that most vaccines produced using the conventional method are relatively crude preparations of inactivated tissue culture grown virus. This tissue cultural mix may cause serious side effects such as allergic responses and abortions in susceptible stock.

There are newer forms of FMDV vaccines that do not use inactivated virus. They are synthetic peptide vaccines and recombinant protein vaccines. The identification of the immuno-dominant sites on viral protein 1 (VP1) of FMDV provided new ideas for designing synthetic peptide and recombinant protein FMD vaccines. Compared to conventional vaccines, these two types of vaccines are both safe in production and application. They are also very easy to handle, store, transport and can be designed to meet specific requirements.

The study of synthetic FMDV peptide vaccine was started by polymerizing the 141 a.a.-160a.a. peptide from VP1 with either glutaraldehyde or air-oxidized after a cysteine residue was added at each terminus. It was found that uncoupled peptides could be made immunogenic. In 1987, Francis and his colleagues reported that the presence of C-terminal cysteines with a free thiol group largely enhanced the immunogenicity of free 141-160 a.a. peptide. Similar results were also obtained when multiple cysteine residues were added. It was suggested that the presence of a free thiol cysteine residue would allow the formation of peptide dimers leading to a more ordered secondary structure causing immune complex formation in vivo (Francis, 1995). According to this idea, immunogenicity of tandem repeats (Cys 137-162(x2)) was compared to that of a single copy of Cys 137-163 peptide. It was found that tandem repeats of the FMDV peptide were generally more immunogenic than the single copy of disulphide dimers. The addition of a cysteine residue could result in the formation of disulphide tetramer structures, which improved the immune response further.

The concept of multiple copies synthetic peptides was further tested by using Tam's multiple antigenic peptide (MAP) system (Tam 1988). This system allows solid phase synthesis of a peptide antigen onto a branching lysine backbone to produce several polylysine octamer constructs. This system where there are multiple copies of the peptide resulted in greatly enhanced response.

In order to apply multiple copies of the FMDV peptide, recombinant DNA technology has been applied by fusing small peptide sequences to the gene coding for larger proteins. These larger proteins of recombinant vaccine have a number of characteristics. The goal of linking the peptide to the carrier is to provide a completely uniform and defined structure for the presentation of the immunogens as compared with those prepared by chemical cross-linking (Francis, 1991). This approach was first investigated by fusing single or multiple copies of the FMDV immunogenic peptides to the N-terminus of a bacterial protein, beta-galactosidase (Broekhuijsen et al., 1986; Winther et al., 1986). Beta-galatosidase was chosen because it has been shown that antibodies can be elicited against the epitopes from VP1 that are located at the N-terminus, and it also contains several T cell epitopes (Krzych et al., 1982; Manca et al., 1985). The immunogenicity of this multiple copy FMDV peptide-beta-galactosidase recombinant protein is found to be similar to that obtained from using the lysine background system (Broekhuijen et al., 1987).

Multiple peptide presentation was then further developed using FMDV peptide sequence fused to the N-terminus of the hepatitis B virus core antigen (HBcAg) to produce HBc fusion particles. It was reported that this 27 nm hybrid protein particle was able to give full protection to guinea pigs with results that were close to that elicited by inactivated FMDV VP1 142 a.a.-160 a.a. peptide and could protect animals against challenge infections.

Although initially promising, the synthetic peptide approach and recombinant protein vaccine approach appear to have shortcomings. Among these are poor predictability of the tertiary structure and weak immunogenicity. Peptides in solution exist in conformations that may not be always optimal for receptor binding (B-cell receptor and possibly T-cell receptor and major histocompatibility gene products) if specific conformation at the three-dimensional level is required for it to exhibit its intended functions.

In the case in which synthetic peptides that are relatively small in size, they tend to be easily degraded in the body after injection. Therefore, they may not be very effective in providing long term immune response probably because the recombinant protein vaccine fails to exhibit a proper conformation. Also, peptide synthesis is expensive which may lead to high production cost of the vaccine. As mentioned, presentation of the FMDV epitopes on peptide vaccines can be achieved by fusing them to the N-terminus of microbial proteins like beta-galactosidase or HBcAg. However, using beta-galactosidase may elicit a lot of additional and undesirable immune responses (Bona et al., 1994). After repetitive immunization of this recombinant protein vaccine, side effects may occur such as immediate hypersensitivity that can cause severe hay fever and asthma in the animal.

Nucleic acid vaccines or DNA vaccine represent a new approach to the control of infectious agents. These novel vaccines are easier to design and manufacture. Recombinant DNA technology is used to clone DNA sequences encoding the protein or proteins to be used as immunogens into an eukaryotic expression vector.

Antigenized antibodies are antibodies, which are genetically engineered in their variable domains to express epitopes of different antigens. Antigenized antibodies can be used as immunogens that focus the immune response on specific B- or T-cell epitopes. As such, antigenized antibodies can be used as an alternative approach to conventional or synthetic peptide vaccination.

Therefore, an effective kind of vaccine that offers both the possibilities of safety and efficiency is the antigenized antibody vaccine. The process of antibody antigenization consists of grafting peptide epitopes derived from antigens other than immunoglobulins into complementarity determining region ("CDR") loops of an antibody molecule. Because the CDR loops are exposed at the surface of the antibody molecule, they provide the major contribution to antibody antigenicity. Unlike the synthetic vaccines described above, antigenized antibodies target antigen-presenting cells via the Fc receptor, thereby maximizing antigen presentation by class II major hisocompatibility (MHC) molecules. Also, antigenized antibodies provide B-cells with a continuous source of antigenic peptides for presentation in class I MHC molecules. In addition to immunogenicity at the B-cell level, antigenized antibodies act as processed peptide products to generate Th-cell immunogenicity.

SUMMARY OF INVENTION

The present invention can be used against FMD in swine, although by using FMDV viral epitopes for cows linked to cow IgG, this vaccine can be applied in other animals like cows as well.

The present invention may be used in a vaccine delivered in four different forms, namely two constructs of protein vaccine and two correlative constructs of DNA vaccine counterparts. All forms of this vaccine deliver the functions of immunization against FMD and FMDV in swine. To be specific, the vaccine in its protein forms are an antigenized antibody vaccine; this peptide sequence contains FMDV epitopes that replace CDR loops in swine IgG or a chimeric protein which FMDV single or tandem repeat epitopes carried by swine IgG heavy chain constant region protein.

As an example shown, the particular FMDV epitopes used for grafting into CDR was engineered. The first form of the DNA counterpart that corresponds to the first form of the protein vaccine utilizes FMDV epitope cDNA sequences as the carrier for single IgG in plasmid form. The second form of the DNA counterpart that corresponds to the second form of the protein vaccine utilizes FMDV epitope DNA sequences linked differently with the heavy chain constant region of swine Ig cDNA. Further, immunization methods of swine against FMD or FMDV are carried out by the use of this vaccine. There are different ways in which this vaccine can be administered. For the protein forms of the vaccine, it can be, for example, administered through conventional injection. In the case of administering the vaccine in its DNA forms, it can be carried out by using epidermis gene gun or injection.

BRIEF DESCRIPTION OF THE DRAWINGS

FIG. 3 shows the amino acid sequence (SEQ ID NO: 1) of the antigenized antibody heavy chain molecule in which the CDR3 region is replaced with FMDV VP1 aa 200 to 213 (SEQ ID NO: 19);

FIG. 4 shows the corresponding cDNA sequence (SEQ ID NO: 2) of the amino acid mentioned in FIG. 3;

FIG. 5 shows the amino acid sequence (SEQ ID NO: 3) of the antigenized antibody heavy chain molecule in which the CDR3 is replaced with FMDV VP1 aa 141 to 160 (SEQ ID NO: 23);

FIG. 6 shows the corresponding cDNA sequence (SEQ ID NO: 4) of the amino acid mentioned in FIG. 5;

FIG. 7 shows the cDNA sequence (SEQ ID NO: 5) of antigenized chimeric vaccine molecule. The bold part shows the nucleotide sequence encoding the epitopes of FMDV VP1 (aa 141 to 160, aa 200 to 213; SEQ ID NO: 22). The rest of the sequence belongs to PIG IgG heavy chain constant region.

FIG. 8 shows the protein sequence (SEQ ID NO: 6) of antigenized chimeric vaccine molecule. The bold part shows the epitopes of FMDV VP1 aa 141 to 160, aa 200 to 213

(SEQ ID NO: 24). The rest of the sequence belongs to PIG IgG heavy chain constant region.

FIG. 9 shows the four amino acid sequences (SEQ ID NO: 7, SEQ ID NO: 8, SEQ ID NO: 9, and SEQ ID NO: 10) of which the IgG light chain in FIG. 8 can be coded for. The bolded sequences are the framework regions. The underlined sequences are the CDR regions. The CDR2 or CDR3 sequence could be replaced by correspondence FMDV epitope sequences.

FIGS. 10A-10D show the four cDNA sequences (SEQ ID NO: 11, SEQ ID NO: 12, SEQ ID NO: 13, and SEQ ID NO: 14) corresponding to the cDNA sequences of the IgG light chain in FIG. 8.

Figure 11A:
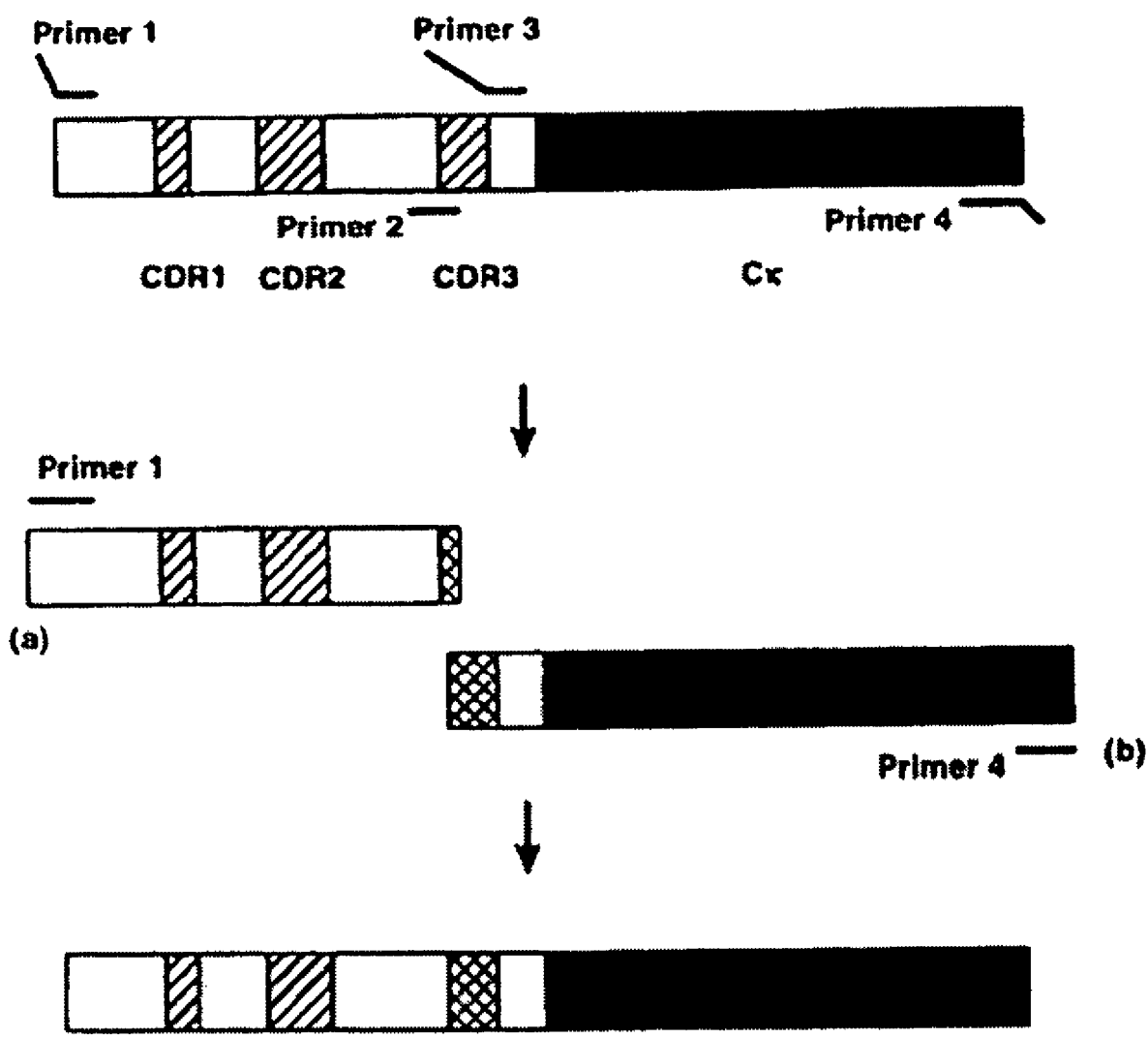
Figure 11B:
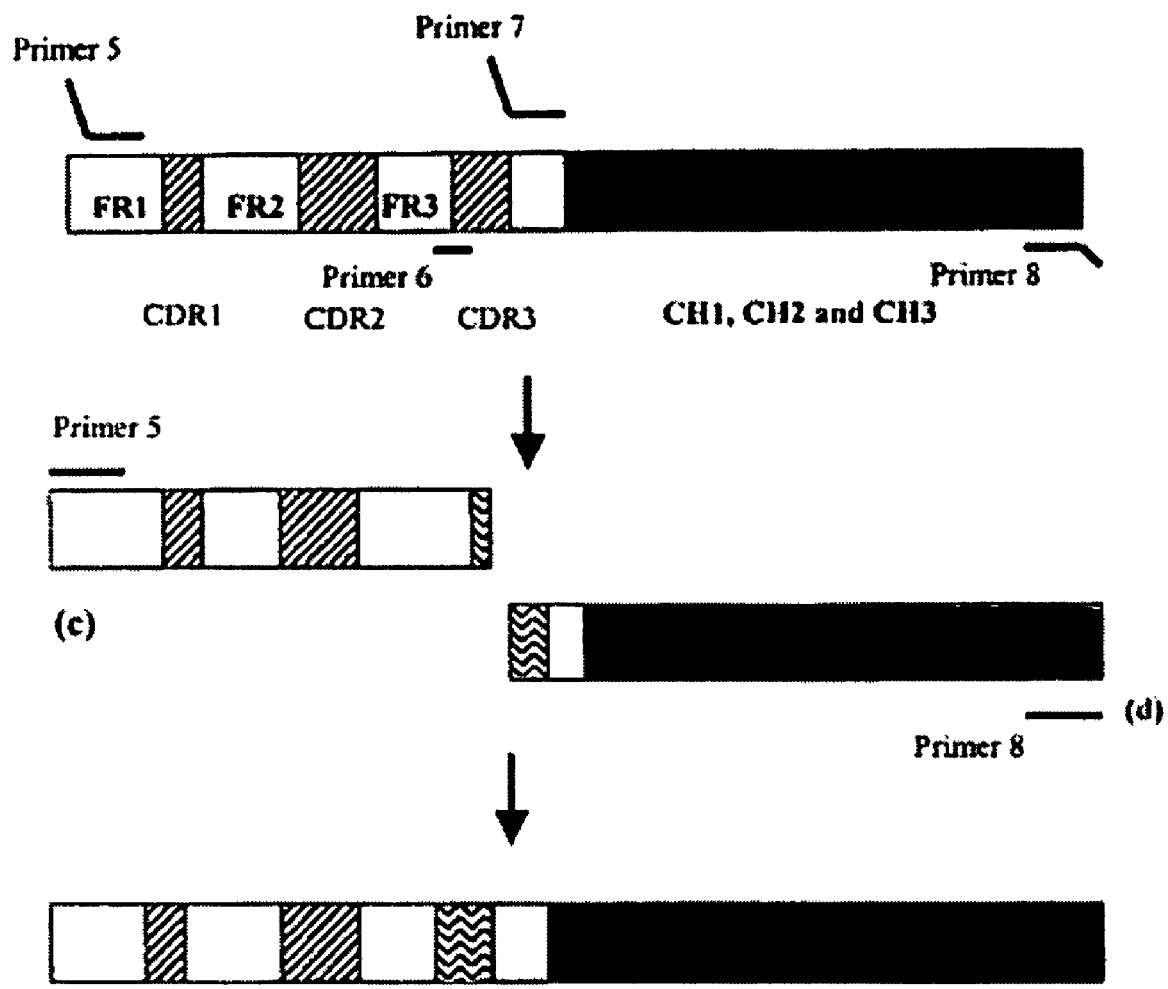

FIG. 11A shows the overlapping (extension) PCR taking place;

FIG. 11B shows the overlapping (extension) PCR taking place.

DETAILED DESCRIPTION OF THE INVENTION

Embodiments illustrated the claims herein elicit an immune response against FMD. One embodiment contains an engineered cDNA sequence encoding for FMDV epitopes. The protein sequence also contains swine IgG cDNA construct as a carrier for the FMDV epitopes. The conjugation of the FMDV epitopes and swine IgG in its protein forms are carried out by grafting of FMDV peptide epitopes into swine IgG CDR loops or link FMDV epitopes with the swine IgG constant region as shown in FIG. 1B.

Figure 1A:
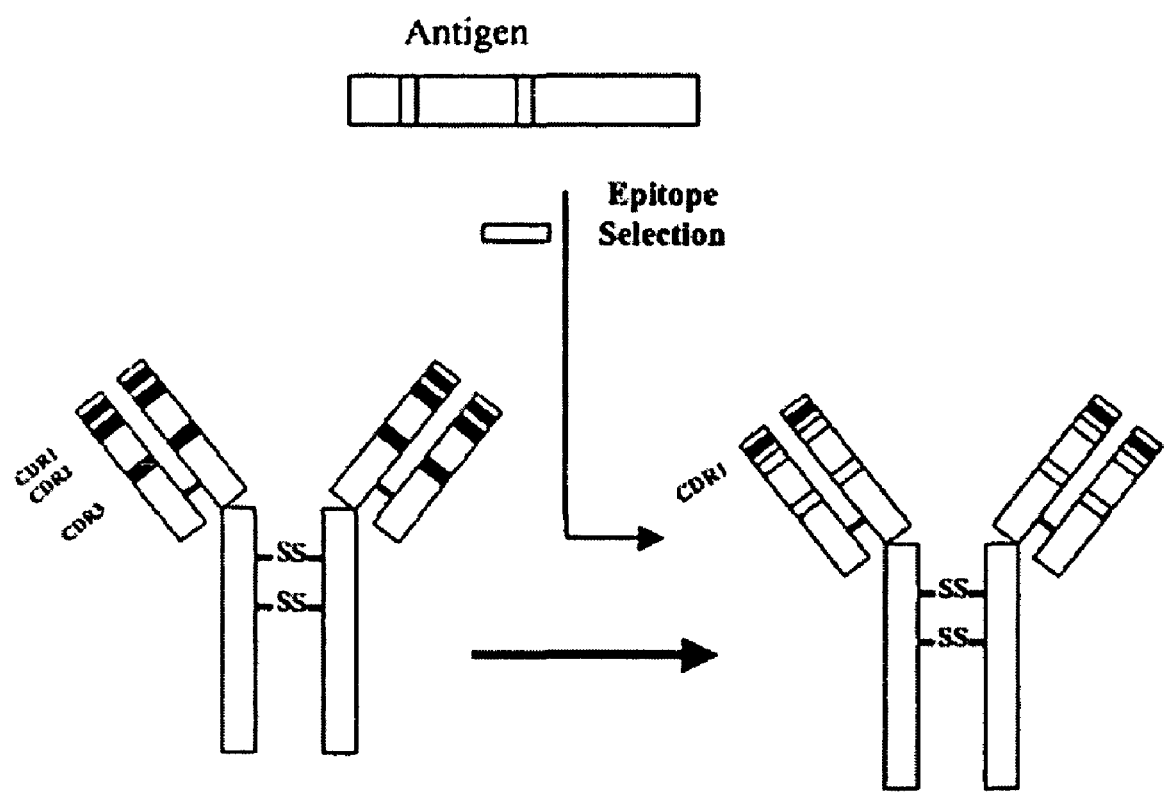
FIG. 1A shows the diagrammatic structure of the antigenized antibody vaccine using swine IgG.
Figure 1B:
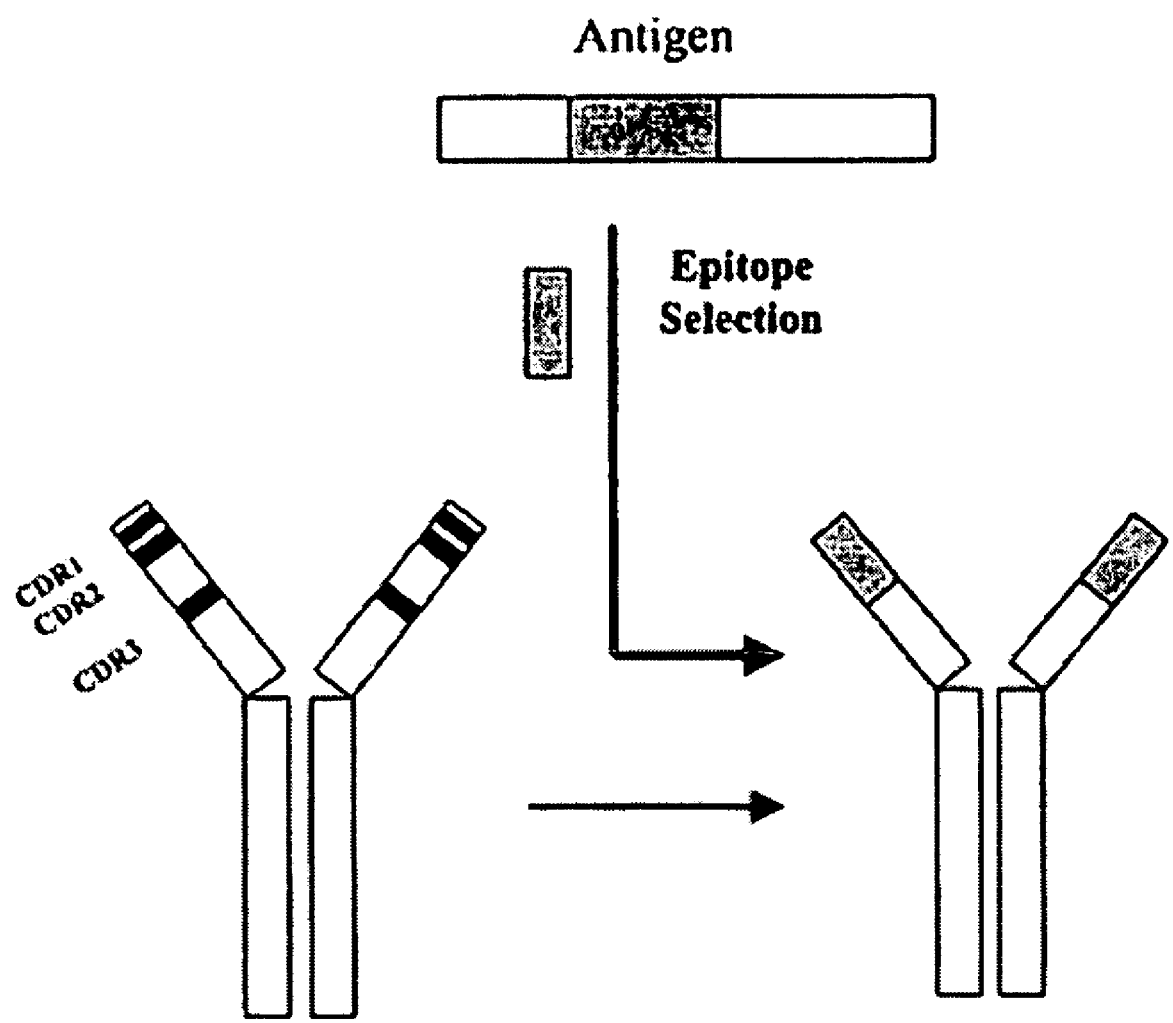
FIG. 1B shows the diagrammatic structure of the antigenized chimeric vaccine using FMDV single or tandem repeat epitopes.
Figure 2A:
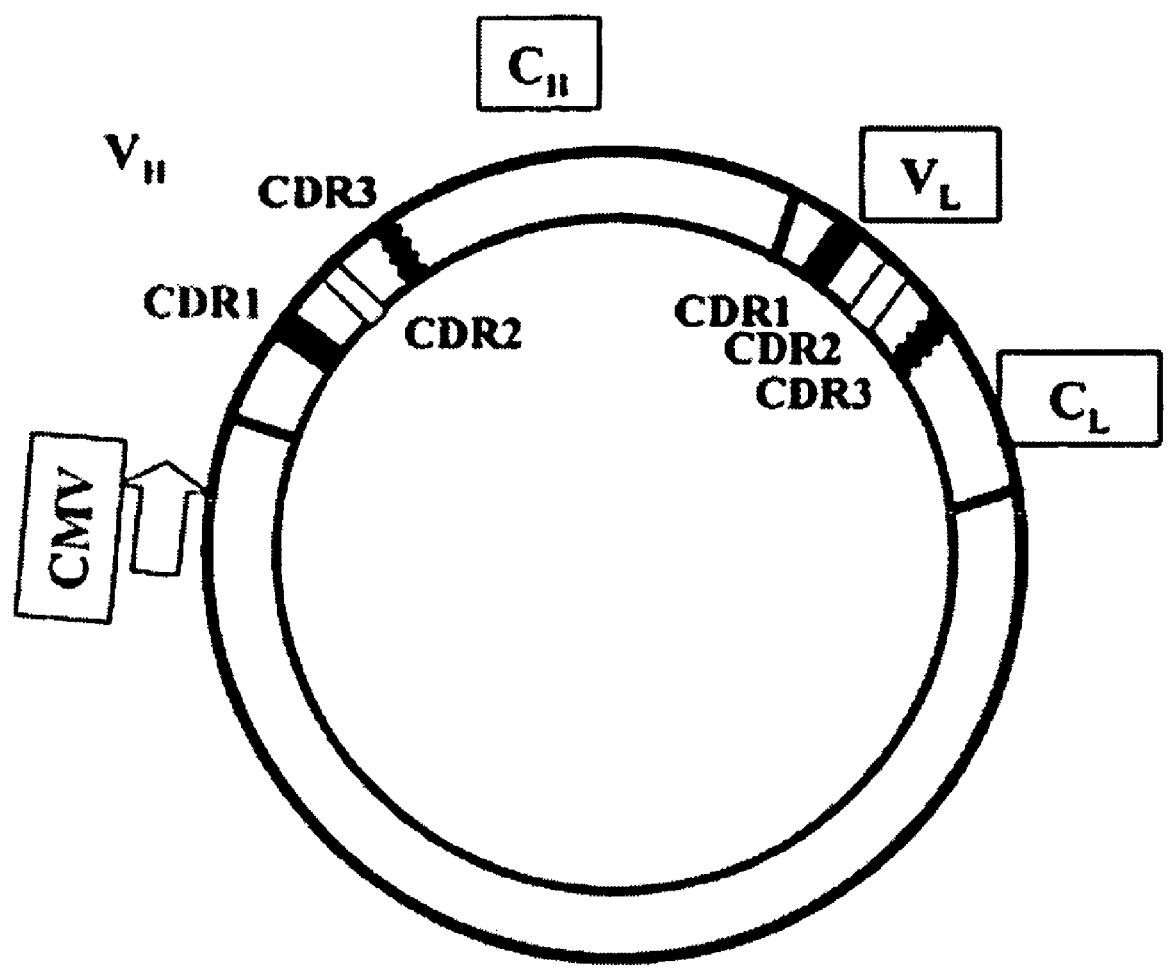
FIG. 2A shows the corresponding cDNA of the antigenized antibody vaccine, which uses IgG cDNA as a carrier in the plasmid.
Figure 2B:
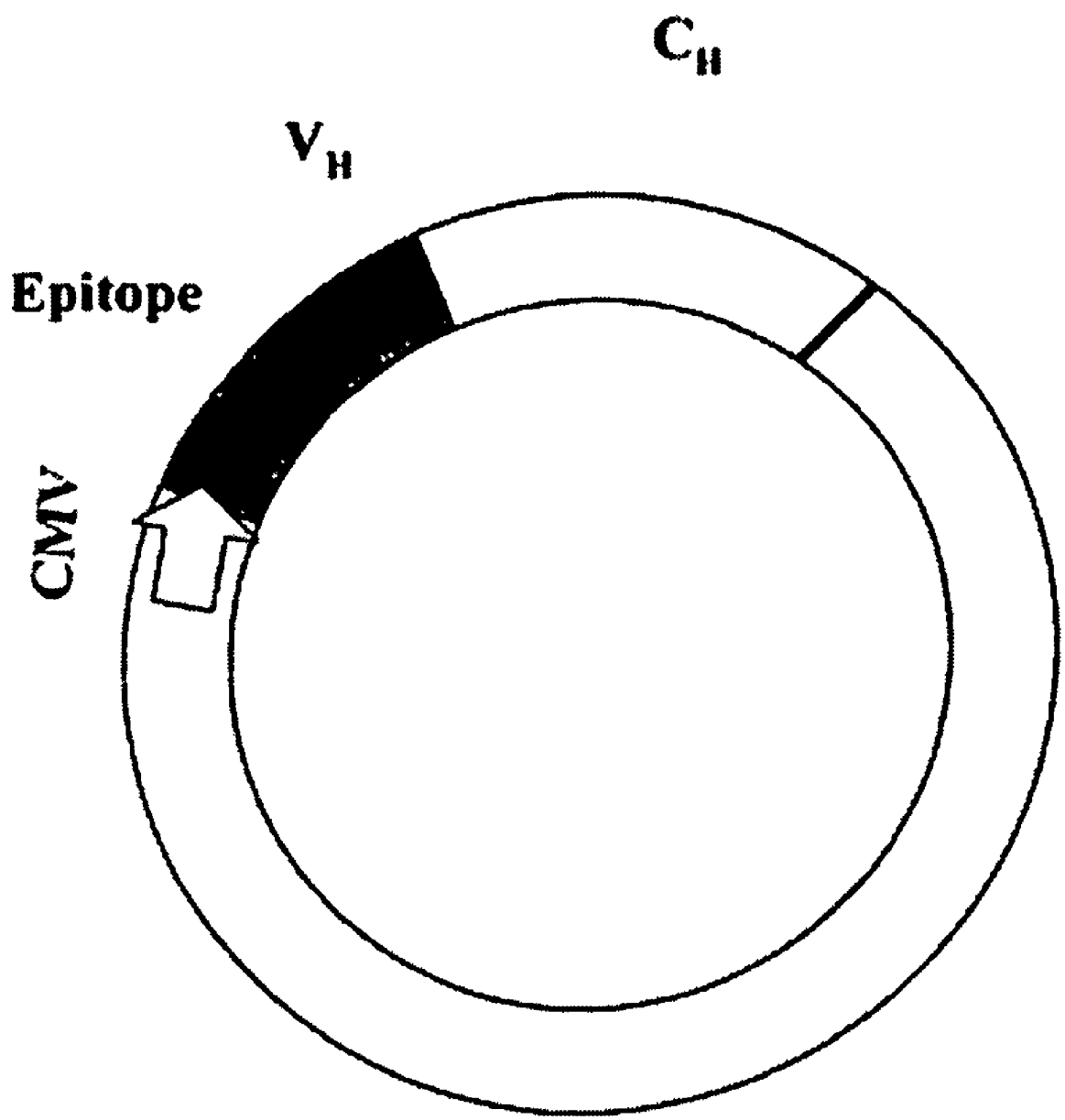
FIG. 2B shows the corresponding cDNA of the antigenized chimeric vaccine using FMDV single or tandem repeat epitopes.

Therefore, the antigenized antibody molecules in its protein form are created from the grafting of peptide epitopes derived from FMDV into swine antibody CDR loops, as shown in FIGS. 1A and 1B. FMDV peptide epitopes were synthesized by PCR based on VP1 gene of FMDV. The overlapping PCR method was used to insert the FMDV peptide epitopes into the CDR regions of swine immunoglobulin heavy and light chain genes. The resulting antigenized antibody genes were cloned into mammalian expression vector. The plasmids were transfected into CHO or myeloma cells.

Four different embodiments are illustrated in FIGS. 1A, 1B, and FIGS. 2A, 2B. Two of them are protein forms (FIGS. 1A, 1B), known as antigenized antibody vaccines that can be administered by injection. The first type is an antigenized antibody vaccine that utilizes swine IgG protein as the carrier for FMDV epitopes and is injected into swine muscle tissue. The first form of this antigenized antibody vaccine (FIG. 1A) inserts the FMDV epitopes into the CDR2 and CDR3 regions of both heavy and light chains swine IgG. The second form of this antigenized antibody vaccine (FIG. 1B) utilizes single or tandem-repeat FMDV epitopes linked to only the heavy chain constant region of swine IgG, forming a chimeric protein. Hence, the second form of this antigenized antibody vaccine can also be called as antigenized chimeric vaccine.

Two other embodiments describe naked DNA vaccines, which can be administered through gene gun shooting. Each DNA form has a corresponding protein form counterpart. There are two forms of this naked DNA vaccine that corresponds to their protein counterparts as mentioned above. The two DNA forms will be expressed by the host's cell machinery after being administered. The corresponding protein equivalents will be directly administered into the animal, which have the same functions as the naked DNA vaccine forms. The first form of this naked DNA vaccine grafts FMDV epitope DNA sequences onto the CDR2 and CDR3 regions of both heavy and light chain swine IgG cDNA. The second form of this DNA vaccine utilizes FMDV epitope DNA sequences (FIG. 4) linked only with the heavy chain constant region of swine IgG cDNA. The two forms of naked DNA vaccine will exhibit the functions of the two forms of antigenized antibody vaccine respectively, when the transcription and translation process produce the products within the host cell machinery.

METHODS

The preparation of the claimed protein sequences involves three major steps, namely 1) cloning of the swine single IgG heavy chain constant region, and swine light chain 2) joining of the two FMDV immunogenic sequences and 3) joining of the swine IgG single heavy chain constant region with the FMDV immunogenic sequence, then inserting it into bacterial expression vector. Detailed procedures are explained as follow.

1) Cloning of the Swine Single IgG Heavy Chain Constant Region

The extraction and purification of mRNA from swine spleen was done by using a commercially available kit (mRNA Preparation kit, by Pharmacia). The procedures were followed as described by the manufacturer. In brief, 3 g of fresh swine spleen was homogenized in 1.2 ml Extraction Buffer. The homogenized tissue extract was diluted by 2.4 ml Elution Buffer and was mixed thoroughly. The homogenate was transferred to a sterile tube and centrifuged for one minute to obtain cleared homogenate. 1 ml of the cleared homogenate was placed on the top of the Oligo(dT)-Cellulose pellet. The Oligo(dT)-Cellulose was resuspended by inverting the tube for 3 minutes. The pellet was collected by centrifugation at 16,000×g for 10 seconds. For washing, the Oligo(dT)-Cellulose was washed five times with 1 ml High-Salt Buffer and centrifuged at 16,000×g for 10 seconds, followed with washing three times with 1 ml Low-Salt Buffer and centrifuged at 16,000×g for 10 seconds. Then the pellet was resuspended in 0.3 ml Low-Salt Buffer and transferred to a MicroSpin™ Column. The column was centrifuged at full speed for 5 seconds. The effluent was discarded and a new collection tube was put in place. This step was repeated twice. The column was placed in a sterile microcentrifuge tube and 0.2 ml pre-warmed Elution Buffer was added. The eluate containing mRNA was collected by centrifugation at full speed for 5 seconds. 10 ml of Glycogen Solution and ¹⁄₁₀ volume of Potassium Acetate Solution was added to the sample. The sample was mixed with 500 ml 100% ethanol and placed at −20° C. for at least 30 minutes. The precipitated mRNA was collected by centrifugation at 14,000 rpm at 4° C. for 5 minutes The supernatant was discarded and the precipitated mRNA was dissolved in DEPC-treated water. The quantity of RNAs was determined by UV absorbance at 260 nm.

RT-PCR Analysis

The cDNA fragments encoding the constant region of the heavy chain of the swine IgG were amplified by RT-PCR using a set of swine IgG 5' and 3' specific primers. Swine IgG 3' specific primers were used to prime the first strand cDNA synthesis from total RNA. Reverse transcription was carried out at 37° C. for 60 minutes by MMLV reverse transcriptase and terminated at 70° C. for 15 minutes. The cDNA products were amplified by PCR in the presence of swine IgG 5' specific primer. The PCR settings were as follows and ran for 30 cycles: denaturing at 94° C. for 1 min, annealing at 50° C. for 1 min and extension at 72° C. for 2 min, with a final extension at 72° C. for 6 min. The PCR products were fractionated on 1.0% low melting agarose gel and the band with sizes corresponding to the constant region of the IgG heavy chain was purified from the gel using phenol:chloroform extraction and ethanol precipitation. The DNA was then ligated to the FMDV immunogenic sequences (F1) later.

The PCR primers used were designed from swine IgG genes (Kacskovics et al., 1994) and the sequence of the primers are as listed below:

```
Swine IgG 3' specific primer
(SEQ ID NO: 15)
5'GAC GCT CGA GTC ATC ATT TAC CCT GAG T 3'

Swine IgG 5' specific primer
(SEQ ID NO: 16)
5'AGC TAA GCT TGC CCC CAA GAC GGC CCC A 3'
```

2) Joining of the two FMDV Immunogenic Sequences

Two oligonucleotide sequences were made corresponding to the residues 141-160 and 200-213 (two sequences were made with residues 155-160 sequence as overlapping region) on the VP1 of FMDV (Kurz et al., 1981). The two sequences were joined by overlapping PCR. The setting was as follows and ran for 5 cycles: 94° C. for 1 minute, 63° C. for 3 minutes. Two primers, VP1 3' primer and VP1 5'primer, were used to add in one Hind III restriction site at the 3' end and one Nde I restriction site at the 5'end. The PCR setting was as follow and ran for 24 cycles: denaturing at 94° C. for 1 minute, annealing at 50° C. for 1 minute, extension at 72° C. for 2 minutes and final extension at 72° C. for 6 minutes. The PCR product was analyzed on 1.5% low melting agarose gel. Product with correct size was cut and purified. The joined fragment was called FMDV-immuno-sequence. The VP1 3' and 5' primers used were designed from VP1 141a.a.-160a.a. and 200a.a.-213a.a. (Kurz et al., 1981). Sequences of the primers are as listed below:

```
VP1 5' primer (SEQ ID NO: 17)
5' ATG CCA TAT GGT ACC AAA C 3'

VP1 5' primer (SEQ ID NO: 18)
5' ATG CAA GCT TCA ACT TCT G 3'
```

FIG. 11A illustrates the overlap (extension) PCR taking place in two stages. First, the CDR1/CDR2 region is amplified, as is the CH/CDR3 region. The oligonucleotides at CDR3 are complementary; the longer primer 3 also contains VP1 141-160 or 200-213 residues. This permits fusion of these two products (a and b) in a subsequent PCR. FIG. 11B illustrates the overlap (extension) PCR takes place in two stages. First, the CDR1/CDR2 region is amplified, as is the CH/CDR3 region. The oligos at CDR3 are complementary; the longer primer 7 also contains VP1 141-160 or 200-213 residues. This permits fusion of these two products (c and d) in a subsequent PCR.

3) Linking of the Swine IgG Single Heavy Chain Constant Region, the FMDV-Immuno-Sequence Fragment and the Bacterial Expression Vector The above fragment was digested with Nde I and Hind III; the swine single IgG heavy chain constant region was digested with Hind III and Xho I, and the bacterial expression vector was digested with Nde I and Xho I. The three digested fragments were purified by phenol/chloroform extraction and ethanol precipitation. They were then ligated by using T4 DNA ligase at 16° C. overnight. The ligation product was transformed into JM109 and colonies were screened by mini-plasmid isolation and then by restriction enzyme digestion. Plasmid from correct clone was isolated and checked by DNA sequencing. Finally, the correct plasmid was transformed into *E. coli* BL(21)DE3pLysE. The plasmid was named as pF1-IgG.

Thus, the present invention can provide an antigenized antibody vaccine against Foot-and-Mouth disease to provide a safer, more cost efficient and/or more effective vaccine product, which can overcome some of the disadvantages of the prior art.

The invention as described is deemed to incorporate equivalents to the integers recited where such equivalents would be apparent to those skilled in the art. The description is provided by way of example and is not to be considered limited to the scope of the invention which is defined in the appended claims.

The invention claimed is:

1. An antigenized swine antibody for Foot-and-Mouth Disease Virus (FMDV) comprising a swine antibody heavy chain, wherein said heavy chain comprises an amino acid sequence selected from the group consisting of: SEQ ID NO: 19; SEQ ID NO:23; and SEQ ID NO:24 in the variable region.

2. The antibody according to claim 1, wherein said swine antibody heavy chain consists of SEQ ID NO: 1.

3. The antibody according to claim 1, wherein said swine antibody heavy chain consists of SEQ ID NO: 3.

4. The antibody according to claim 1, wherein said swine antibody heavy chain consists of SEQ ID NO: 6.

5. The antibody according to claim 1, further comprising a modified light chain of swine IgG.

6. The antibody of claim 5, wherein the light chain comprises a complementarity determining region (CDR) sequence, wherein said light chain comprises an amino acid sequence selected from the group consisting of SEQ ID NO: 7, SEQ ID NO:8, SEQ ID NO:9 and SEQ ID NO:10.

7. A method of preparing an antigenized swine antibody for Foot-and-Mouth Disease (FMD) comprising the steps:

a) cloning a first nucleotide sequence encoding the heavy chain constant region of swine IgG;

b) joining a second nucleotide sequence encoding one or more epitopes of Foot-and-Mouth Disease Virus (FMDV) to the first nucleotide sequence, whereby the resulting nucleotide sequence encodes a protein selected from the group consisting of: SEQ ID NO: 19, SEQ ID NO:23 and SEQ ID NO:24; and c) expressing said cloned nucleotide sequence to produce the swine antibody.

8. The method according to claim 7, wherein said swine antibody heavy chain consists of SEQ ID NO: 1.

9. The method according to claim 7, wherein said swine antibody heavy chain consists of SEQ ID NO: 3.

10. The method according to claim 7, wherein said swine antibody heavy chain consists of SEQ ID NO: 6.

11. The method according to claim 7, further comprising the step of expressing a third nucleotide sequence encoding a modified light chain.

12. The method of claim 11, whereby the third nucleotide sequence encodes an amino acid sequence selected from the group consisting of SEQ ID NO: 7, SEQ ID NO:8, SEQ ID NO:9 and SEQ ID NO:10.

* * * * *